(12) United States Patent
Taylor-Fishwick

(10) Patent No.: US 9,914,910 B2
(45) Date of Patent: Mar. 13, 2018

(54) METHODS OF PRESERVING AND PROTECTING PANCREATIC BETA CELLS AND TREATING OR PREVENTING DIABETES BY INHIBITING NOX-1

(71) Applicant: Eastern Virginia Medical School, Norfolk, VA (US)

(72) Inventor: David Taylor-Fishwick, Norfolk, VA (US)

(73) Assignee: Eastern Virginia Medical School, Norfolk, VA (US)

( * ) Notice: Subject to any disclaimer, the term of this patent is extended or adjusted under 35 U.S.C. 154(b) by 0 days.

(21) Appl. No.: 15/475,518

(22) Filed: Mar. 31, 2017

(65) Prior Publication Data

US 2017/0275591 A1    Sep. 28, 2017

Related U.S. Application Data

(62) Division of application No. 14/776,132, filed as application No. PCT/US2014/029717 on Mar. 14, 2014, now Pat. No. 9,688,960.

(60) Provisional application No. 61/783,777, filed on Mar. 14, 2013.

(51) Int. Cl.
| | | |
|---|---|---|
| A01N 43/42 | (2006.01) | |
| A61K 31/44 | (2006.01) | |
| C12N 5/071 | (2010.01) | |
| A61K 31/437 | (2006.01) | |
| A61K 31/444 | (2006.01) | |
| A01N 1/02 | (2006.01) | |
| A61K 31/5415 | (2006.01) | |
| A61K 31/713 | (2006.01) | |
| A61K 45/06 | (2006.01) | |
| C07D 279/20 | (2006.01) | |
| C07D 471/04 | (2006.01) | |
| C12N 15/113 | (2010.01) | |

(52) U.S. Cl.
CPC ......... *C12N 5/0676* (2013.01); *A01N 1/0226* (2013.01); *A61K 31/437* (2013.01); *A61K 31/444* (2013.01); *A61K 31/5415* (2013.01); *A61K 31/713* (2013.01); *A61K 45/06* (2013.01); *C07D 279/20* (2013.01); *C07D 471/04* (2013.01); *C12N 15/1137* (2013.01); *C12N 2310/14* (2013.01); *C12N 2320/30* (2013.01); *C12N 2501/999* (2013.01)

(58) Field of Classification Search
CPC .................................................. A61K 31/437
USPC ....................................................... 514/303
See application file for complete search history.

(56) References Cited

U.S. PATENT DOCUMENTS

| | | |
|---|---|---|
| 8,563,500 B2 | 10/2013 | Guelow et al. |
| 2008/0039420 A1 | 2/2008 | Juhasz et al. |
| 2010/0048560 A1 | 2/2010 | Page et al. |
| 2010/0273854 A1 | 10/2010 | Kalinski et al. |
| 2010/0305187 A1 | 12/2010 | Guelow et al. |
| 2013/0123256 A1 | 5/2013 | Page et al. |
| 2013/0267578 A1 | 10/2013 | Kalinski et al. |

FOREIGN PATENT DOCUMENTS

WO    WO-2013/106547    7/2013

OTHER PUBLICATIONS

Cifuentes-Pagano et al., "NADPH oxidase inhibitors: a decade of discovery from Nox2ds to HTS," Cell. Mol. Life Sci., vol. 69, No. 14, pp. 2315-2325 (2012).

(Continued)

*Primary Examiner* — Jeffrey H Murray
(74) *Attorney, Agent, or Firm* — Wilmer Cutler Pickering Hale and Dorr LLP

(57) ABSTRACT

Methods of preserving and/or protecting pancreatic beta cells by inhibiting NOX-1. In a further aspect, NOX-1 inhibitors are administered to a subject in order to preserve and/or protect beta cells in the prevention or treatment of diabetes. NOX-1 inhibitors are also disclosed.

11 Claims, 18 Drawing Sheets

(56) References Cited

OTHER PUBLICATIONS

Gianni et al., "Optimization and Characterization of an Inhibitor for NADPH Oxidase 1 (NOX-1)," Probe Reports from the NIH Molecular Libraries Program, National Center for Biotechnology Information, pp. 1-35 (2010).
International Search Report and Written Opinion for International Application No. PCT/US14/29717 dated Aug. 20, 2014 (10 pages).
Jaquet et al., "Small-Molecule NOX Inhibitors: ROS-Generating NADPH Oxidases as Therapeutic Targets," Antioxidants & Redox Signaling, vol. 11, No. 10, pp. 2535-2552 (2009).
Koulajian et al., "NADPH oxidase inhibition prevents beta cell dysfunction induced by prolonged elevation of oleate in rodents," Diabetologia, vol. 56, No. 5, pp. 1078-1087 (2013).
Laleu et al., "First in Class, Potent, and Orally Bioavailable NADPH Oxidase Isoform 4 (Nox4) Inhibitors for the Treatment of Idiopathic Pulmonary Fibrosis," Journal of Medicinal Chemistry, vol. 53, No. 21, pp. 7715-7730 (2010).
Lambeth et al., "NOX enzymes as novel targets for drug development," Semin. Immunopathol., vol. 30, No. 3, pp. 339-363 (2008).
Sancho and Fabregat, "The NADPH oxidase inhibitor VAS2870 impairs cell growth and enhances TGF-β-induced apoptosis of liver tumor cells," Biochemical Pharmacology, vol. 81, No. 7, pp. 917-924 (2011).
Taylor-Fishwick, "NOX, NOX who is there?, The contribution of NADPH Oxidase One to beta cell dysfunction," Frontiers in Endocrinology, vol. 4, No. 40, pp. 1-8 (2013).
Weaver and Taylor-Fishwick, "Regulation of NOX-1 expression in beta cells: A positive feedback loop involving the Src-kinase signaling pathway," Molecular and Cellular Endocrinology, vol. 369, No. 1-2, pp. 35-41 (2013).
Weaver et al., "Integration of pro-inflammatory cytokines, 12-lipoxygenase and NOX-1 in pancreatic islet beta cell dysfunction," Molecular and Cellular Endocrinology, vol. 358, No. 1, pp. 88-95 (2012).

METHODS OF PRESERVING AND PROTECTING PANCREATIC BETA CELLS AND TREATING OR PREVENTING DIABETES BY INHIBITING NOX-1

CROSS REFERENCE TO RELATED APPLICATION

This application is a divisional of U.S. application Ser. No. 14/776,132, filed Sep. 14, 2015, which is the National Stage of International Application No. PCT/US14/029717, filed Mar. 14, 2014, which claims the benefit of U.S. Provisional Application No. 61/783,777, filed Mar. 14, 2013, the contents of each of which are hereby incorporated by reference.

SEQUENCE LISTING

The instant application contains a Sequence Listing which has been submitted electronically in ASCII format and is hereby incorporated by reference in its entirety. Said ASCII copy, created on Jun. 13, 2017, is named 113019_284US3_SL.txt and is 1,350 bytes in size.

FIELD

The present application is directed to methods of preserving and/or protecting pancreatic beta cells by inhibiting NOX-1. In a further aspect of this invention, NOX-1 inhibitors are administered to a subject in order to preserve and/or protect beta cells in the prevention or treatment of diabetes. NOX-1 inhibitors are disclosed herein.

BACKGROUND

Diabetes is a disease derived from multiple causative factors and characterized by elevated levels of plasma glucose (hyperglycemia) in the fasting state. There are two main forms of diabetes mellitus: (1) insulin dependent or Type 1 diabetes and (2) non-insulin-dependent or Type II diabetes. A decrease in β-cell mass occurs in both Type I and Type II diabetes.

Conventional methods for treating diabetes have included administration of fluids and insulin in the case of Type 1 diabetes and administration of various hypoglycemic agents in Type II diabetes. Unfortunately, many of the known hypoglycemic agents exhibit undesirable side effects and toxicities.

Thus, for both type 1 and type 2 diabetes there is a need for development of agents capable of stimulating insulin secretion that are effective and well-tolerated for use in therapeutic methods and formulations. Beta cell dysfunction and loss of functional beta cell mass is a principle contributor to the development of diagnosable diabetes. Current therapeutic options do little to halt or reverse a loss of beta cell function. There remains a clinical need to develop new strategies for beta cell preservation and protection.

SUMMARY

In one aspect, the present application describes a method to preserve and protect β-cell function. The method includes contacting a population or preparation of β-cells, islets, or pancreatic cells with an inhibitor of NADPH oxidase-1.

In another aspect, the present application relates in part to a method of treating a subject for diabetes, the method comprising administering a therapeutically effective amount of a NOX-1 inhibitor to the subject.

In some embodiments, the NOX-1 inhibitor is a phenothiazine or a pyrazolopyridine dione compound.

In yet another aspect, the present application relates in part to a method for increasing insulin secretion by a cell or in a tissue or animal, by administering to the cell, tissue or animal an effective amount of an inhibitor of a NOX-1. In some embodiments the animal is a human.

In still another aspect, the present application also relates in part to a method for improving glucose tolerance or treating impaired glucose tolerance in an animal in need thereof, comprising administering to the animal an effective amount of an inhibitor of NOX-1.

In some embodiments of the disclosed methods, the NOX-1 inhibitor can be coadministered in combination with one or more additional therapeutic agents, such as an agent known in the art for treatment of diabetes or for having anti-hyperglycemic activities.

In some embodiments of the disclosed methods the NOX-1 inhibitor can be coadministered with TD26 (Betatrophin) or a functional portion thereof, or with an insulin receptor antagonist.

In accordance with certain embodiments, the present invention relates to a method to reduce beta cell/islet apoptosis in diabetes. In accordance with another aspect, the method disclosed herein can be used to preserve beta cell/islet survival in vitro, ex vivo, or in vivo in cells exposed to stressful stimuli including but not limited to inflammation, inflammatory cytokines, high glucose, or elevated free fatty acids.

In accordance with another aspect, a method to preserve beta cell and islet survival by disruption of 12-lipoxygenase signaling is disclosed (see Weaver et al (2012) *Mol. Cell. Endo.* 358(1): 88-95, the content of which is hereby incorporated by reference).

BRIEF DESCRIPTION OF THE DRAWINGS

(FIG. 12A) Pro-caspase-3 cleavage was measured in isolated primary mouse islets treated with pro-inflammatory cytokine cocktail (PIC) in absence or presence of ML171 for 4 hours. (FIG. 12B) Glucose-stimulated insulin secretion was assessed in untreated (Ctl) islets or islets treated with PIC with or without 10 μM ML171. Insulin secretion was measured in islets exposed to 1 mM glucose (L, grey bars) or 16 mM glucose (H, black bars). (FIG. 12C) Expression of NOX-1 gene is shown in primary mouse islets treated with PIC without or with 1 μM ML171 for 24 hours. Data shows fold expression relative to untreated islets. * p<0.05, ** p<0.01 relative to Ctl, # p<0.05, ## p<0.01 relative to PIC and n=3.

DETAILED DESCRIPTION OF THE INVENTION

Figure 1:
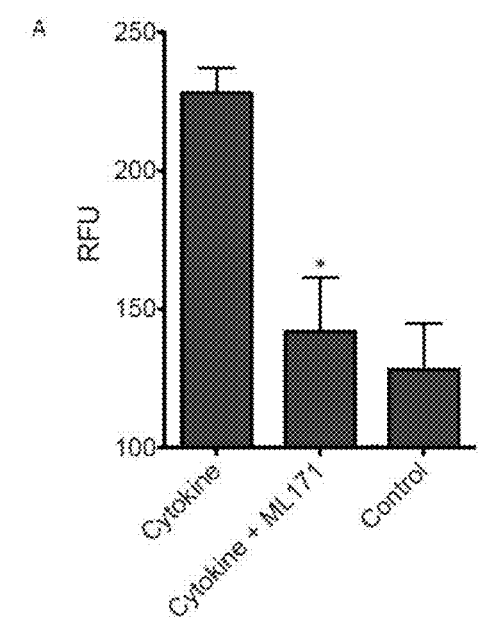
FIG. 1 is a plot of detected relative fluorescent units (RFU) as a function of treatment of primary mouse islets.

The present application is directed to a method to preserve and protect β-cell function. The method includes contacting a population or preparation of islets or β-cells with an inhibitor of NADPH oxidase-1 (NOX-1). In another aspect, the present application relates in part to a method of treating a subject for diabetes, the method comprising administering a therapeutically effective amount of a NOX-1 inhibitor to the subject. In accordance with certain embodiments, the NOX-1 inhibitor is a phenothiazine or a pyrazolopyridine dione compound.

NADPH Oxidase Enzymes

A loss of functional beta cell mass is an underlying feature of diabetes. Oxidative stress is a recognized contributing factor to beta-cell failure. Relative to other cells, beta-cells are particularly sensitive to sustained elevation in intracellular reactive oxygen species (ROS) and resultant oxidative stress. Limited capacity for free-radical detoxification in beta-cells results from low activity of enzymes such as catalase, superoxide dismutase, and glutathione peroxidase.

Further, beta-cells are less efficient in correcting DNA damage arising from oxidative stress. Several serum conditions associated with diabetes are recognized to induce cellular ROS. These include elevated inflammatory cytokines, increased levels of free fatty acids, and high plasma glucose concentration. Sources of cellular ROS in the beta-cell include endoplasmic reticulum stress, mitochondria stress and NAPDH oxidase activity. NADPH oxidase enzymes are multi-protein complexes; the role of which is the generation of reactive oxygen species including superoxide ($O_2.-$) and hydroxyl radical (.OH). This is distinct to mitochondrial or endoplasmic reticulum stress where ROS generation is a byproduct of physiological activity. Seven members in the NADPH oxidase family have been identified, termed NOX-1 through -5 and DUOX-1/-2. In recent years, catalytic subunits and required associated proteins for NOX-1, NOX-2 and NOX-4 have been reported to be expressed in beta-cells. Physiologically, NADPH oxidase activity in beta-cells has been linked with glucose-stimulated insulin secretion (GSIS). Pathophysiologically, sustained NADPH oxidase activity may contribute to stimuli-induced beta-cell dysfunction associated with diabetes development and progression.

Inflammation-induced beta-cell dysfunction is recognized as a feature of type 1 diabetes and type 2 diabetes. In response to inflammatory cytokine exposure the present application describes a selective upregulation of NOX-1 in islets from mice or humans and murine beta-cells. Inflammatory cytokine stimulation of beta-cells and islets induced a loss of glucose-stimulated insulin secretion, an increase in intracellular ROS, and an induction of apoptosis. These outcomes of pro-inflammatory cytokine stimulation were concomitant with an elevated expression of NOX-1. Expression of NOX-1 in beta-cells involves a feedforward regulation with responsiveness to elevated intracellular ROS and redox signaling.

In terms of beta-cell dysfunction a feed-forward regulation of NOX-1 following stimuli induction could result in a sustained chronic increase in intracellular ROS and progression to damaging oxidative stress. Inhibition of NOX-1 activity or NOX-1 feed-forward regulation provides a candidate target to preserve beta-cell function in an inflammatory environment. Lack of selective inhibitors of NADPH oxidases has provided a barrier to interpret the functional importance of NOX isotypes. Prior accepted inhibitors, apocynin and diphenylene iodonium are non-selective, exhibiting activity between NOX-isotypes and on other falvoenzymes. Recent high throughput screening-based campaigns have identified new small molecules with selective inhibitory activity for NOX enzymes. The inhibitor ML171, a 2-acetylphenothiazine compound, is a nanomolar inhibitor of NOX-1 with greater than thirtyfold selectivity over other NOX isotypes. ML171 inhibits NOX-1 activity in human colon cancer cells, and its inhibition is overcome with overexpression of NOX-1 thus supporting the target selectivity of ML171.

The present application describes the selective chemical inhibition of NOX-1 in islets and beta cells using the phenothiazine inhibitor ML171. The contribution of NOX-1 to beta-cell dysfunction induced by pro-inflammatory cytokines has been assessed and the viability for targeted inhibition of NOX-1 to protect and preserve beta-cells in an inflammatory environment has been determined.

NOX-1 Inhibitors

A NOX-1 inhibitor useful in a method described herein includes a molecule that modulates NOX-1 activity at the enzyme level (e.g., by binding directly to NOX-1), at the transcriptional and/or translational level (e.g., by preventing NOX-1 gene expression), and/or by other modes (e.g., by binding to a substrate or co-factor of NOX-1, or by modulating the activity of an agent that directly or indirectly modulates NOX-1 activity, i.e., NOX-1 modulators)). For example, in some embodiments, a NOX-1 agent is a compound that modulates the activity of an endogenous NOX-1 inhibitor. The NOX-1 agent can be any, including, but not limited to, a chemical compound, a protein or polypeptide, a peptidomimetic, or a nucleic acid such as antisense oligonucleotide, siRNA, ribozyme and apatamer. A number of structurally diverse molecules with NOX-1 inhibitory activity are known in the art. A NOX-1 inhibitor can act directly against NOX-1, or indirectly in connection with a co-factor, substrate, or other molecule.

NOX-1 inhibitors also include siRNA for NOX-1. Examples of other NOX-1 inhibitors include other agents that inhibit interleukin 12 or interleukin 23 production or STAT4 signaling, such as STA5326 (apilimod—structure below (6-morpholino-N-((E)-m-tolylmethyleneamino)-2-(2-(2-pyridyl)ethoxy)pyrimidin-4-amine)).

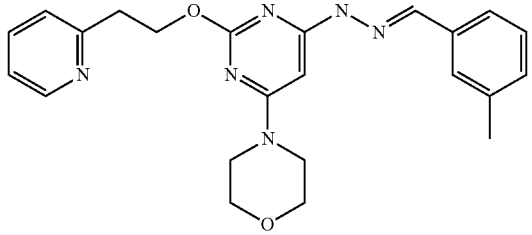 [SMILES: Cc1cccc(/C=N/Nc2cc(N3CCOCC3)nc(OCCc3ccccn3)n2)c1]

Specific examples of NOX-1 inhibitors useful herein include, but are not limited to, phenothiazine and pyrazolopyridine dione compounds. Examples of useful phenothiazine compounds and derivatives are disclosed in U.S. Pat. No. 4,666,907, the contents of which are hereby incorporated by reference. Compounds of the present invention include in particular those selected from the following group:

1-acetyl-4-methyl-2-phenyl-5-(pyridin-3-ylmethyl)-1H-pyrazolo[4,3-c]pyridine-3,6(2H,5H)-dione;
tert-butyl 4-{[4-methyl-3,6-dioxo-2-phenyl-5-(pyridin-3-ylmethyl)-2,3,5,6-tetrahydro-1H-pyrazolo[4,3-c]pyridin-1-yl]carbonyl}piperidine-1-carboxylate;
1-(methoxyacetyl)-4-methyl-2-phenyl-5-(pyridin-3-ylmethyl)-1H-pyrazolo[4,3-c]pyridine-3,6(2H,5H)-dione;
4-methyl-1-(4-phenoxybutanoyl)-2-phenyl-5-(pyridin-3-ylmethyl)-1H-pyrazolo[4,3-c]pyridine-3,6(2H,5H)-dione;
1-[(3-methoxyphenyl)acetyl]-4-methyl-2-phenyl-5-(pyridin-3-ylmethyl)-1H-pyrazolo[4,3-c]pyridine-3,6(2H,5H)-dione;
acetyl-4-methyl-2-(2-methylphenyl)-5-(pyridin-2-ylmethyl)-1H-pyrazolo[4,3-c]pyridine-3,6(2H,5H)-dione; and
1-acetyl-2-(2-chlorophenyl)-4-methyl-5-(pyridin-2-ylmethyl)-1H-pyrazolo[4,3-c]pyridine-3,6(2H,5H)-dione.

A particularly useful compound is 2-acetylphenothiazine (ML171) having the structure shown below:

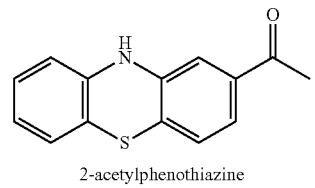 [SMILES: CC(=O)c1ccc2c(c1)Nc1ccccc1S2]

2-acetylphenothiazine

ML171 is a potent and selective inhibitor of NOX1. It is not cytotoxic and is selective among NOX family members NOX2, NOX3, and NOX4, as well as against xanthine oxidase.

The following publications disclose additional compounds that may be suitable as NOX1 inhibitors in accordance with the methods disclosed herein. These publications are hereby incorporated by reference. Lambeth et al., NOX enzymes as novel targets for drug development, *Semin Immunopathol* (2008) 30:339-63; Jaquet et al., Small-Molecule NOX Inhibitors: ROS-Generating NADPH Oxidases as Therapeutic Targets, *Antioxidants & Redox Signaling*, (2009) 11:2535-51; Gianni et al., Optimization and Characterization of an Inhibitor for NADPH Oxidase 1 (NOX-1), *Molecular Libraries,* 2010 Oct. 13 [Updated 2011 Dec. 12]. In: Probe Reports from the NIH Molecular Libraries Program [Internet]. Bethesda (Md.): National Center for Biotechnology Information (US); 2010. Available from: http://www.ncbi.nlm.nih.gov/books/NBK98925/; Cifuentes-Pagano et al., NADPH oxidase inhibitors: a decade of discovery from Nox2ds to HTS, *Cell. Mol. Life Sci.* 69, 2315-2325; Laleu et al., First in Class, Potent, and Orally Bioavailable NADPH Oxidase Isoform 4 (Nox4) Inhibitors for the Treatment of Idiopathic Pulmonary Fibrosis, *J. Med. Chem.,* (2010) 53: 7715-30); Weaver and Taylor-Fiswhwick, Regulation of NOX-1 expression in beta cells: A positive feedback loop involving Src-kinase signalling pathway, *Mol. And Cell. Endocrinology* 369 (2013) 35-41; Taylor-Fishwick, NOX, NOX Who is There? The Contribution of NADPH Oxidase One to Beta Cell Dysfunction, *Front. Endocrinol.* 2013; 4:40. Examples of NOX-1 inhibitors also include Aryliodonium compounds, such as Diphenyleneiodonium (DPI), VAS2870 (3-benzyl-7-(2-benzoxazolyl)thio-1,2,3-triazolo[4,5-d]pyrimidine)

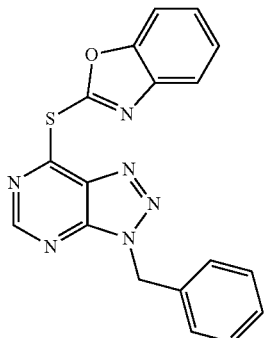

3-benzyl-7-(2-benzoxazolyl)thio-
1,2,3-triazolo[4,5-d]pyrimidine

GKT 136091 having the following structure:

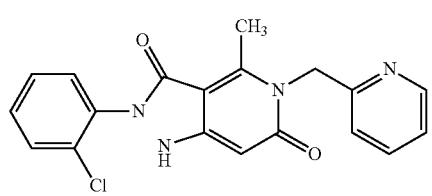

GKT 137831 having the following structure:

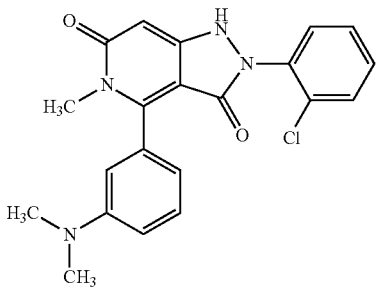 [SMILES: CN(C)c1cccc(-c2c3c(=O)n(-c4ccccc4Cl)[nH]c3cc(=O)n2C)c1]

NCTT-1 having the following structure:

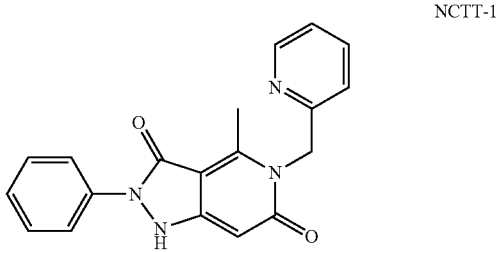 [SMILES: Cc1c2c(=O)n(-c3ccccc3)[nH]c2cc(=O)n1Cc1ccccn1]

In some embodiments of this and other aspects of the invention, activity of NOX-1 is inhibited or lowered by at least 5%, at least 10%, at least 20%, at least 30%, at least 40%, at least 50%, at least 60%, at least 70%, at least 80%, at least 90%, at least 95%, at least 98%, or 100% (e.g., complete loss of activity) relative to an uninhibited control.

In some embodiments, the NOX-1 inhibitor has the desired activity at a concentration that is lower than the concentration of the inhibitor that is required to produce another, unrelated biological effect. In some exemplary embodiments, the concentration of the inhibitor required for NOX-1 inhibitory activity is at least about 2-fold lower, or at least about 5-fold lower, or at least about 10-fold lower, or at least about 20-fold lower than the concentration required to produce an unrelated biological effect.

In some embodiments of this and other aspects of the invention, the NOX-1 inhibitor has an IC50 of less than or equal to 500 nM, less than or equal to 250 nM, less than or equal to 100 nM, less than or equal to 50 nM, less than or equal to 10 nM, less than or equal to 1 nM, less than or equal to 0.1 nM, less than or equal to 0.01 nM, or less than or equal to 0.001 nM.

As used herein, the term "pancreatic cells" refers to cells, or a population, or preparation of cells of pancreatic tissues, which can include both endocrine and exocrine tissues, as well as cell lines derived therefrom. The endocrine pancreas is composed of hormone producing cells arranged in clusters known as islets of Langerhans. Of the four main types of cells that form the islets ("islet cells"), the alpha cells produce glucagons, the beta cells produce insulin, the delta cells produce somatostatin, and the PP cells produce pancreatic polypeptide (PP). The exocrine pancreas includes the pancreatic acini and the pancreatic duct. Pancreatic acinar cells synthesize a range of digestive enzymes. Ductal cells secrete bicarbonate ions and water in response to the hormone secreted from the gastrointestinal tract. Therefore, the term "pancreatic cells" includes cells found in a pancreas, including alpha cells, beta cells, delta cells, PP cells, acinar cells, ductal cells, mesenchymal cells, fibroblasts and other cells present in the pancreatic connective tissue, or other cells (e.g., endothelial cells, neuronal cells, and progenitor cells that are not differentiated or not fully differentiated or yet to be differentiated), or a mixture or combination thereof.

As used herein, "pancreatic cell" includes primary pancreatic cells, pancreatic cell-like cells derived from dedifferentiated cells, e.g., from induced pluripotent stem cells (iPSCs), or pancreatic cell-like cells that have been directly reprogrammed from a cell of endodermal origin (e.g., a liver cell or an exocrine pancreatic cell). In one embodiment, the pancreatic cell is not an immortalized cell line (i.e., one which proliferates indefinitely in culture). In one embodiment, the pancreatic cell is not a transformed cell, i.e., a cell that exhibits a transformation property, such as growth in soft agar, or absence of a contact inhibition.

In some embodiments, the pancreatic cells are from pancreatic endocrine tissues. In some embodiments, the pancreatic cells are within islet of Langerhans. The term "islet" or "islets" as used herein includes the constituent cell types within the islet of Langerhans, including alpha, beta, delta, and epsilon cells, intact islets, islet fragments or combinations thereof.

In some embodiments, the pancreatic cells are in a stabilized state, e.g., the cells were taken from a subject and treated in such a manner as to allow them to be stored for some period of time. For example, the cells can be frozen, e.g., using methods known in the art for freezing primary cells, such that the cells are viable when thawed. For example, methods known in the art to freeze and thaw embryos to generate live mammals can be adapted for use in the present methods. Such methods may include the use of liquid nitrogen, e.g., with one or more cryoprotectants, e.g., agents that prevent freeze-thaw damage to the cell.

A cell population, e.g., a pancreatic, islet, of β cell population, can be contacted with the compounds, e.g., NOX-1 inhibitors described herein in a cell culture e.g., in vitro or ex vivo, or the compound can be administered to a subject, e.g., in vivo. In some embodiments of the invention, a compound described herein can be administered to a subject to treat, and/or prevent a disorder which is caused by a reduction in function and/or number of β-cells, e.g., hyperglycemia or diabetes. The term "ex vivo" refers to cells which are removed from a living organism and cultured outside the organism (e.g., in a test tube).

The term "contacting" or "contact" as used herein in connection with contacting a population of cells, e.g. a population of pancreatic, islet, or β cells includes, subjecting the cells to an appropriate culture media which comprises the indicated compound or agent. Where the cell population is in vivo, "contacting" or "contact" includes administering the compound or agent in a pharmaceutical composition to a subject via an appropriate administration route such that the compound or agent contacts the cell population in vivo.

For in vivo methods, a therapeutically effective amount of a compound described herein can be administered to a subject. Methods of administering compounds to a subject are known in the art and easily available to one of skill in the art.

Promoting β-cell replication in a subject can lead to treatment, prevention or amelioration of a number of disorders which are caused by a reduction in function and/or number of β-cells, e.g., hyperglycemia or diabetes. Without wishing to be bound by theory, increasing β-cell replication in a subject leads to an increase in density and/or number of β-cells, e.g., β-cell mass.

As used herein, an increase in β-cell mass refers to an increase in number of β-cells, e.g. an increase in number of β-cells (e.g., pancreatic β-cells) in a subject being treated with a compound described herein as compared to the number of β-cells in the subject prior to the onset of treatment. The increase in β-cell mass can be at least 5%, 10%, 20%, 30%, 40%, 50%, 50%, 70%, 80%, 90%, 1-fold, 2-fold, 5-fold, 10-fold, 50-fold, 100-fold or more in treated subject compared to the β-cell mass in the subject prior to onset of treatment.

Pancreatic cells suitable for use in ex vivo methods can be prepared from a pancreas according to methods well known to those skilled in the art. For example, the harvested pancreas can be incubated with an enzyme solution at or about 37° C. to digest the pancreatic tissue into small clusters of tissue and cells. Following the appropriate digestion time the tissue digest can be filtered to remove large undigested tissue. The digested tissue may then can be applied to a density gradient such as Ficoll, polysucrose, dextran, and the like. The density gradient can either be continuous or discontinuous. The tissue loaded density gradient can then be centrifuged, and the cells contained within the digest migrate within the gradient according to their density. The cells can be retrieved from the gradient, washed, and placed in culture. Pancreatic cells prepared in this manner can contain multiple cell types.

For ex vivo methods, pancreatic cells can include autologous pancreatic cells, i.e., a cell or cells taken from a subject who is in need of additional β-cells (i.e., the donor and recipient are the same individual). Autologous pancreatic cells have the advantage of avoiding any immunologically-based rejection of the cells. Alternatively, the cells can be heterologous, e.g., taken from a donor. The second subject can be of the same or different species. Typically, when the cells come from a donor, they will be from a donor who is sufficiently immunologically compatible with the recipient, i.e., will not be subject to transplant rejection, to lessen or remove the need for immunosuppression. In some embodiments, the cells are taken from a xenogeneic source, i.e., a non-human mammal that has been genetically engineered to be sufficiently immunologically compatible with the recipient, or the recipient's species. Methods for determining immunological compatibility are known in the art, and include tissue typing to assess donor-recipient compatibility for HLA and ABO determinants. See, e.g., Transplantation Immunology, Bach and Auchincloss, Eds. (Wiley, John & Sons, Incorporated 1994). In some embodiments, pancreatic cells are recombinant β-cells, for example those described in U.S. Pat. Nos. 6,114,599; 6,242,254; and 6,448,045, contents of which are herein incorporated by reference in their entirety.

The methods disclosed herein may also be utilized in the preparation of viable xenotransplantable porcine islets and/or the treatment of a mammalian patient (including humans) suffering from diabetes involving the transplantation into the mammal of viable porcine islets capable of producing insulin within the host. Piglet islets are candidates for xenotransplantation of piglet islets with cytokines (PIC; TNF, IL-1, IFN) induced expression of NOX-1 protein. Co-treatment with 1 μM ML171 reduces PIC-induced NOX-1 protein. Islets were treated for 18 hours. Data supports feedforward regulation of NOX-1 expression and effective uncoupling of this pathway in piglet islets by inhibition of NOX-1 activity.

These methods are known to those skilled in the art as evidenced by U.S. Pat. No. 8,142,769, contents of which are herein incorporated by reference in their entirety.

In some embodiments, the subject suffers from Type I, Type 1.5 or Type 2 diabetes or has a pre-diabetic condition.

After ex vivo contact with a compound described herein, when the pancreatic cells, e.g., β-cells, have reached a desired population number or density, e.g., about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, or more cells, the cells can be transplanted in a subject who is in need of additional β-cells. The cells can be transplanted in a subject from whom the cells were originally obtained or in different subject. Methods for surgically removing and transplanting suitable pancreatic cells, e.g., beta-cells, from a mammal are known in the art; see, e.g., Shapiro et al., N. Engl. J. Med. 343(4):230-8 (2000); Ryan et al., Diabetes 50(4):710-9 (2001).

Since the methods described herein can increase β-cell mass, the methods described herein are useful in treating disorders associated with a loss of β-cells or β-cell mass, e.g., hyperglycemia or diabetes. The methods can include administering a NOX-1 inhibitor to the subject. The inhibitors can be administered systemically or locally, e.g., by injection or implantation of a device that provides a steady dose of the inhibitor to the pancreatic tissues, e.g., to the islets. Such devices are known in the art, and include micro-pumps and controlled-release matrices, e.g., matrices that breakdown over time, releasing the modulator into the tissue.

A NOX-1 inhibitor can be administered to a subject either as a monotherapy or as a combination therapy with other pharmaceutically active agents. Exemplary pharmaceutically active compounds include, but are not limited to, those found in Harrison's Principles of Internal Medicine, 13th Edition, Eds. T. R. Harrison et al. McGraw-Hill N.Y., N.Y.; Physicians Desk Reference, 50th Edition, 1997, Oradell N.J., Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's The Pharmacological Basis of Therapeutics; and current edition of The Merck Index, the complete contents of all of which are incorporated herein by reference.

The NOX-1 inhibitor and the pharmaceutically active compound can be co-administered to a subject. As used herein, the term "co-administration" refers to administration of two or more biologically active substances to a subject. Co-administration can be simultaneous or sequential. The two or more biologically active substances can be part of a single composition or separate compositions. For example, the NOX-1 inhibitor and the pharmaceutically active agent can be administered to the subject in the same pharmaceutical composition or in different pharmaceutical compositions (at the same time or at different times). For example, when administered in separate pharmaceutical compositions or formulations, a NOX-1 inhibitor can be administered first followed by the pharmaceutically active agent. In other embodiments, the pharmaceutically active agent can be administered first followed by a NOX-1 inhibitor. A NOX-1 inhibitor can be administered within 1 minute, within 2 minutes, within 5 minutes, within 10 minutes, within 15 minutes, within 30 minutes, within 45 minutes, within 1 hour, within 2 hours, within 3 hours, within 4 hours, within 5 hours, or within 6 hours of each other.

In some embodiments, a combination therapy as disclosed herein comprises co-administration of a NOX-1 inhibitor with one or more blood glucose lowering agents or agents that are beneficial to beta cells. These agents include, but are not limited to, Metformin or other Biguanides, DPP4 inhibitors, Sulfonylureas or Metiglitinides, SGLT2 inhibitors, Glucokinase activators, Thiazolidinediones, PPARdelta agonists, non-activating PPARgamma modulators, Glp-1 analogs, GIP analogs, Glp-1-receptor agonists, combined Glp-1/GIP receptor agonists, FGF21, agonistic FGFR monoclonal antibodies, Oxyntomodulin analogs, IAPP analogs, Leptin or Leptin analogs, Adiponectin or Adiponectin analogs, Insulin or Insulin analogs, proton pump inhibitors or gastrin receptor agonists, Reg family proteins/Reg family protein derived peptides or alpha-glucosidase inhibitors. Further, they can be administered together with pharmaceutical agents which have an immunosuppressive activity, e.g., antibodies, polypeptides and/or peptidic or non-peptidic low molecular weight substances.

In some embodiments, a combination therapy of the present invention comprises co-administration of a NOX-1 inhibitor with an agent that acts additively with Exendin-4 to stimulate insulin secretion when glucose levels are elevated and improve glucose tolerance, i.e., GLP-1 analogs. Exemplary GLP-1 analogs include, but are not limited to, Exendin-4 (a GLP-1 related peptide from the lizard Heloderma suspectum), Liraglutide, Lixisenatide, Albiglutide and Taspoglutide), or any other peptidic agonist of the GLP-1 receptor. Also suitable for co-administration are Oxyntomodulin (a GLP-1 related peptide) and stabilized variants of Oxyntomodulin, as well as GLP-1-receptor/GIP-receptor double agonists. In some embodiments, a combination therapy of the present application comprises co-administration of Dipyridamole and Exendin-4 to improve glucose tolerance more than either Dipyridamole or Exendin-4 alone.

In some embodiments, a combination therapy of the present application comprises co-administration of a NOX-1 inhibitor with an inhibitor of DPP-4. In certain embodiments, the inhibitor of DPP-4 is Alogliptin. In certain embodiments, the inhibitor of DPP-4 is Linagliptin. In certain embodiments, the inhibitor of DPP-4 is Vildagliptin. In certain embodiments, the inhibitor of DPP-4 is Berberine. In certain embodiments, the inhibitor of DPP-4 is Saxagliptin. In certain embodiments, the inhibitor of DPP-4 is Sitagliptin.

The terms "treatment," "treating," "treat," "therapy," "therapeutic," and the like are used herein to refer generally to obtaining a desired pharmacological and/or physiological effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a subject, and includes: (a) preventing the disease or symptom from occurring in a subject which may be predisposed to the disease or symptom, may or may not be diagnosed as having it; (b) inhibiting the disease symptom, i.e., arresting its development; or (c) relieving the disease symptom, i.e., causing regression of the disease or symptom.

The term "pharmaceutically acceptable carrier," as used herein, refers to any and all solvents, dispersion media, coatings, antibacterial and antifungal agent, isotonic and absorption delaying agents for pharmaceutical active substances as are well known in the art. The term "pharmaceutical" or "agent", as used herein, includes biological pharmaceuticals such as proteins, peptides, and oligonucleotides. Except insofar as any conventional media or agent is incompatible with the agent, its use in the therapeutic pharmaceutical compositions is contemplated. Supplementary compounds or biological pharmaceuticals can also be incorporated into the pharmaceutical compositions.

As used herein, the term "excipient" refers to the additives used to convert a synthetic agent into a form suitable for its intended purpose. For pharmaceutical compositions of the present invention suitable for administration to a human, the term "excipient" includes those excipients described in the HANDBOOK OF PHARMACEUTICAL EXCIPIENTS, American Pharmaceutical Association, 2nd Ed. (1994), which is herein incorporated in its entirety. The term "excipients" is meant to include fillers, binders, disintegrating agents, lubricants, solvents, suspending agents, dyes, extenders, surfactants, auxiliaries and the like. Liquid excipients can be selected from various oils, including those of petroleum, animal, vegetable or synthetic origin, such as, peanut oil, soybean oil, mineral oil, sesame oil, hydrogenated vegetable oil, cottonseed oil, groundnut oils, corn oil, germ oil, olive oil, or castor oil, and so forth.

Suitable excipients also include, but are not limited to, fillers such as saccharides, lactose, fructose, sucrose, inositol, mannitol or sorbitol, xylitol, trehalose, cellulose preparations and/or calcium phosphates, tricalcium phosphate or calcium hydrogen phosphate, as well as starch paste, using modified starch, maize starch, wheat starch, rice starch, potato starch, gelatin, tragacanth, ethoxylated isostearyl alcohols, polyoxyethylene sorbitol and sorbitan esters, microcrystalline cellulose, hydroxypropyl cellulose, methyl cellulose, hydroxypropyl methyl cellulose, aluminum metahydroxide, bentonite, sodium carboxymethylcellulose, croscarmellose sodium, crospovidone and sodium starch glycolate, and/or polyvinyl pyrrolidine and mixtures thereof. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries include, silica, stearic acid or salts thereof, such as, magnesium stearate, sodium stearyl fumarate, or calcium stearate.

The expression "therapeutically effective amount" refers to an amount of an agent disclosed herein, that is effective for preventing, ameliorating, treating or delaying the onset of a disease or condition.

The pharmaceutical compositions of the inventions can be administered to any animal that can experience the beneficial effects of the agents of the invention. Such animals include humans and non-humans such as primates, pets and farm animals.

Pharmaceutical Compositions Comprising Agents of the Invention

The present invention also comprises pharmaceutical compositions comprising the NOX-1 inhibitors (i.e., the "agent") disclosed herein. Routes of administration and dosages of effective amounts of the pharmaceutical compositions comprising the agents are also disclosed. The agents of the present invention can be administered in combination with other pharmaceutical agents in a variety of protocols for effective treatment of disease.

The pharmaceutical compositions of the present invention are administered to a subject in a manner known in the art. The dosage administered will be dependent upon the age, health, and weight of the recipient, kind of concurrent treatment, if any, frequency of treatment, and the nature of the effect desired.

In addition to the agents disclosed herein, the pharmaceutical compositions of the present invention may further comprise at least one of any suitable auxiliaries including, but not limited to, diluents, binders, stabilizers, buffers, salts, lipophilic solvents, preservatives, adjuvants or the like. Pharmaceutically acceptable auxiliaries are preferred. Examples and methods of preparing such sterile solutions are well known in the art and can be found in well known texts such as, but not limited to, REMINGTON'S PHARMACEUTICAL SCIENCES (Gennaro, Ed., 18th Edition, Mack Publishing Co. (1990)). Pharmaceutically acceptable carriers can be routinely selected that are suitable for the mode of administration, solubility and/or stability of the agent.

Pharmaceutical excipients and additives useful in the present invention can also include, but are not limited to, proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination in ranges of 1-99.99% by weight or volume. Exemplary protein excipients include serum albumin such as human serum albumin (HSA), recombinant human albumin (rHA), gelatin, casein, and the like. Representative amino acid components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like.

Carbohydrate excipients suitable for use in the present invention include monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), myoinositol and the like.

Pharmaceutical compositions suitable for parenteral administration include aqueous and non-aqueous sterile injection solutions which may contain anti-oxidants, buffers, bacteriostats and solutes that render the formulation isotonic with the blood of the intended recipient; and aqueous and non-aqueous sterile suspensions which may include suspending agents and thickening agents. The pharmaceutical compositions may be presented in unit-dose or multi-dose containers, sealed ampules and vials, and may be stored in a freeze-dried (lyophilized) condition requiring only the addition of the sterile liquid carrier, water for injections, immediately prior to use. Extemporaneous injection solutions and suspensions may be prepared from sterile powders, granules and tablets of the kind previously described.

For parenteral administration, sterile suspensions and solutions are desired. Isotonic preparations which generally contain suitable preservatives are employed when intravenous administration is desired. The pharmaceutical compositions may be administered parenterally via injection of a pharmaceutical composition comprising an agent dissolved in an inert liquid carrier. The term "parenteral," as used herein, includes, but is not limited to, subcutaneous injections, intravenous, intramuscular, intraperitoneal injections, or infusion techniques. Acceptable liquid carriers include, vegetable oils such as peanut oil, cotton seed oil, sesame oil and the like, as well as organic solvents such as solketal, glycerol formal and the like. The pharmaceutical compositions may be prepared by dissolving or suspending the agent in the liquid carrier such that the final formulation contains from about 0.005% to 30% by weight of an agent.

The composition of the invention can also include additional therapeutic agents such as, but not limited to hydrophilic drugs, hydrophobic drugs, hydrophilic macromolecules, cytokines, peptidomimetics, peptides, proteins, toxoids, sera, antibodies, vaccines, nucleosides, nucleotides, nucleoside analogs, genetic materials and/or combinations thereof.

In addition to agents and pharmaceutical compositions of the invention, and additional pharmaceutically active agents, the pharmaceutical formulation can also contain suitable pharmaceutically acceptable carriers comprising excipients and auxiliaries that facilitate processing of the active agents into preparations that can be administered to animals, as described herein.

Pharmaceutical formulations useful in the present invention can contain a quantity of agent(s) according to this invention in an amount effective to treat the condition, disorder or disease of the subject being treated.

The invention is also directed to a kit form useful for administration to patients in need thereof. The kit may have a carrier means being compartmentalized in close confinement to receive two or more container means therein, having a first container means containing a therapeutically effective amount of a pharmaceutical composition of the invention and a carrier, excipient or diluent. Optionally, the kit can have additional container mean(s) comprising a therapeutically effective amount of additional agents.

The kit comprises a container for the separate pharmaceutical compositions such as a divided bottle or a divided foil packet, however, the separate pharmaceutical compositions can also be contained within a single, undivided container. Typically, the kit contains directions for administration of the separate components. The kit form is particularly advantageous when the separate components are preferably administered at different dosage intervals, or when titration of the individual components of the combination is desired by the prescribing physician. The kits of the invention include testing and screening kits and methods, to enable practitioners to measure levels of the active ingredients in bodily fluids. The kits of the invention also include research-grade reagents and kits available for use and purchase by research entities.

Routes of Administration of Pharmaceutical Compositions Comprising the Agents of the Invention The invention further relates to the administration of at least one agent disclosed herein by the following routes, including, but not limited to oral, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarenal, intraretinal, intraspinal, intrasynovial, intrathoracic, intrauterine, intravesical, bolus, vaginal, rectal, buccal, sublingual, intranasal, iontophoretic means, or transdermal means.

Methods of Preparation of Pharmaceutical Compositions of the Present Invention

Methods of preparing various pharmaceutical compositions with a certain amount of active ingredients are known, or will be apparent in light of this disclosure, to those skilled in the art. Methods of preparing said pharmaceutical compositions can incorporate other suitable pharmaceutical excipients and their formulations as described in Remington's Pharmaceutical Sciences, Martin, E. W., ed., Mack Publishing Company, 19th ed. (1995).

One of ordinary skill in the art will appreciate that a method of administering pharmaceutically effective amounts of the pharmaceutical compositions of the invention to a patient in need thereof, can be determined empirically, or by standards currently recognized in the medical arts. The agents can be administered to a patient as pharmaceutical compositions in combination with one or more pharmaceutically acceptable excipients. It will be understood that, when administered to a human patient, the total daily usage of the agents of the pharmaceutical compositions of the present invention will be decided within the scope of sound medical judgment by the attending physician. The specific therapeutically effective dose level for any particular patient will depend upon a variety of factors: the type and degree of the cellular response to be achieved; activity of the specific agent or composition employed; the specific agents or composition employed; the age, body weight, general health, gender and diet of the patient; the time of administration, route of administration, and rate of excretion of the agent; the duration of the treatment; drugs used in combination or coincidental with the specific agent; and like factors well known in the medical arts. It is well within the skill of the art to start doses of the agents at levels lower than those required to achieve the desired therapeutic effect and to gradually increase the dosages until the desired effect is achieved.

Dosaging can also be administered in a patient-specific manner to provide a predetermined concentration of the agents in the blood, as determined by techniques accepted and routine in the art.

Dosage Determinations

In general, the agents disclosed herein may be used alone or in concert with other therapeutic agents at appropriate dosages defined by routine testing in order to obtain optimal efficacy while minimizing any potential toxicity. The dosage regimen utilizing an agent of the present invention may be selected in accordance with a variety of factors including type, species, age, weight, sex, medical condition of the patient; the severity of the condition to be treated; the route of administration; the renal and hepatic function of the patient; and the particular agent employed. A physician or veterinarian of ordinary skill can readily determine and prescribe the effective amount of the drug required to prevent, counter, or arrest the progress of the condition.

In one aspect, the invention provides for a method of increasing β-cell mass or insulin production in a subject, the method comprising: (a) contacting a pancreatic cell, islet, or β-cell with a compound described herein, in a cell culture; (b) allowing the cell to replicate for a time sufficient to produce a desired number or density of cells; and (c) introducing the cells from step (b) into a subject.

The methods by which such cells can be introduced into the subject are described herein. One representative method involves the encapsulation of cells in a biocompatible coating. In this approach, cells are entrapped in a capsular coating that protects the encapsulated cells from immunological responses, and also serves to prevent uncontrolled proliferation and spread of the cells. An exemplary encapsulation technique involves encapsulation with alginate-polylysine-alginate. In particular embodiments, capsules made by employing this technique generally contain several hundred cells and have a diameter of approximately 1 mm.

EXAMPLES

The following examples are presented for the purpose of illustration only and are not intended to be limiting.

Materials and Methods

Mouse Islet Isolation and Human Islets

Human donor islets were obtained from integrated islet distribution project (http://iidp.coh.org) and cultured in CMRL media (Mediatech, Manassas, Va.). Mouse islets were freshly isolated from 8-week old male C57BL/6J mice (Jackson Laboratory, Bar Harbor, Me.) by common bile duct cannulation and collagenase digestion. Islets were hand picked prior to use.

Islets and Cell Lines

INS-1 cells were cultured in RPMI-1640 media (Life Technologies, Grand Island, N.Y.) supplemented with 10% fetal calf serum, 1% penicillin/streptomycin, 10 mM Hepes, 2 mM Lglutamine, 1 mM sodium pyruvate, and 0.05 mM 2-mercaptoethanol at 370 C with 5% $CO_2$.

βTC-3 cells were cultured in DMEM media (Life Technologies, Grand Island, N.Y.) supplemented with 18% fetal calf serum, 1% penicillin/streptomycin, 4 mM L-glutamine, 5.5 mM glucose, and 1 mM sodium pyruvate at 370 C with 5% $CO_2$.

Treatment and RT-PCR

Isolated primary human or mouse islets, or INS-1, βTC-3 cells lines were treated with a proinflammatory cytokine cocktail (PICs) (IL-1β 5 ng/mL, TNF-α 10 ng/mL, and IFN-γ 100 ng/mL, R&D Systems, Minneapolis, Minn.) for 24 hours: 2-acetylphenothiazine (ML171) (EMD Millipore, Billerica, Mass.) was added at the stated concentration 30 minutes prior. Total RNA was isolated using the RNeasy Mini Kit (Qiagen, Valencia, Calif.) and cDNA prepared using MMLV reverse transcriptase (Life Technologies) and random hexamers (Life Technologies). Jump Start Taq polymerase (Life Technologies) was used in PCR reactions. Primers used with SYBR Green 1 (Molecular Probes, Carlsbad, Calif.) probes: NOX-1 forward 5'-CGC TCC CAG CAG AAG GTC GTG ATT ACC AGG G-3' (SEQ ID NO: 1); NOX-1 reverse 5'-GGA GTG ACC CCA ATC CCT GCC CCA ACC A-3' (SEQ ID NO: 2); GAPDH forward 5'-TCA CCA CCA TGG AGA AGG C-3'(SEQ ID NO: 3); GAPDH reverse 5'-GCT AAG CAG TTG GTG GTG CA-3'(SEQ ID NO: 4). RT-PCR reactions were performed in triplicate (CFX96 Bio-Rad, Hercules, Calif.). Taqman primers (Life Technologies) were also used. Data was normalized to the housekeeping gene GAPDH and analyzed using the 2-ΔΔCT method.

Western Blotting

INS-1 or βTC-3 cells were treated with PICs for 24 hours without or with ML171. Cells were then lysed (1× PBS, 1% Triton X-100, 1 mM PMSF, 1 mM Halt Protease Inhibitor Cocktail (Pierce, Rockford, Ill.), 1 mM NaVO4), and incubated on ice for 20 min. Cleared (14,000 rpm, 15 min, 4° C.) lysate was collected. Proteins separated on 10% Tris-glycine gels (Life Technologies) were transferred onto PDVF (Immobilon-FL, Millipore, Billerca, Mass.). Membranes were blocked in TBS/0.05% Tween (Sigma) plus 5% non-fat milk (Bio-Rad) for 1 hr at room temperature before incubation overnight at 40 in primary antibody with gentle shaking. The membrane was washed between antibody cycles four times for 5 min each in TBS/Tween (0.05%). Primary antibodies: 1:250 Anti-NOX-1 or 1:1000 β-actin 1 (Abcam, Cambridge, Mass.).

Signal detected with 1:2000 HRP-secondary antibody for 1 hour (GE Healthcare, Buckinghamshire, UK) SuperSignal Chemiluminescent Substrate (Thermo Scientific, Rockford, Ill.) on a ChemiDoc XRS System (Bio-Rad). Densitometry was determined using Image J (http://rsb-web.nih.gov/i/).

ROS Measurement

Cells treated for 1 hour were then washed with PBS prior to addition of 10 μM 6-Carboxy-2',7'-Dichlorodihydrofluorescein Diacetate, Di(Acetoxymethyl ester) (DCF-DA, Life Technologies) for 30 min at 370 C. Post PBS wash cells were incubated at 370 C for 1 hour. Prior to fluorescence measurement (SpectraMax Molecular Devices, Sunnyvale, Calif.) at excitation 480 nm: emission 530 nm.

Glucose-Stimulated Insulin Secretion (GSIS)

Treated islets or cells then were washed with PBS and placed in 1 mL serum-free Kreb-Ringer buffer (115 mM NaCl, 24 mM NaHCO3, 5 mM KCl, 1 mM MgCl2, and 25 mM HEPES) for 1 hour at 370 C. Low (1 mM) or high (16 mM) glucose was added for 370 C for 30 min. Insulin levels in media were measured by ELISA (Mercodia, Winston Salem, N.C.) as per the manufacturer's instructions.

Apoptosis Detection

A. Caspase-3 Assay: Pro-caspase-3 cleavage was measured using a caspase-3 Assay kit (BD Pharmigen, Franklin Lakes, N.J.) per the manufacturer's instructions; fluorescence being measured (SpectraMax, Molecular Devices, Sunnyvale, Calif.) at excitation 380 nm and emission 440 nm (INS-1) or 460 nm (βTC-3, mouse).

B. Fluorescence microscopy: Stimulated cells or islets were washed in cold PBS, and incubated for 30 mins at 40 C with cold PBS containing 1 μg/mL propidium iodide and 0.1 μM YO-PRO-1 (Life Technologies). For cell lines, five randomly fields per well were analyzed. For islets, all islets (>1000 um2 in size) were analyzed. Densitometric fluorescent value for YO-PRO-1 (green channel) was normalized to background and expressed proportional to cell occupied area (phase contrast). Images captured across three channels with Axiophot (Zeiss, Jena, Germany) with Axiovision (Zeiss) image analysis.

Statistical Analysis

Experiments were performed in triplicate. Students t-test of one-way ANOVA with Tukey post hoc testing were used to determine statistical significance (95% confidence and p<0.05). Prism 4.0 (Graph-Pad Software, Inc., La Jolla, Calif.)

NOX-1 Inhibitor Protects Primary Mouse Islets from Cytokine-Induced Cell Death.

FIG. 1: Treatment of primary mouse islets with inflammatory cytokines (TNFα, IL-1β, IFNγ) induces islet/beta cell death (apoptosis) which can be measured in a fluorescent-based assay (green signal) using YO-PRO-1. These inflammatory cytokines are elevated in diabetes. The degree of cell death can be quantified by measuring the green signal. The graph is a quantitative analysis of multiple (≥4 visual fields in replicate wells). The detected relative fluorescent units (RFU) are plotted. In comparison to control (non-cytokine treated) islets, cytokine stimulation induced cell death. The NOX-1 inhibitor (ML171) at 1 μM protected islets from cytokine induced cell death (*p<0.05).

NOX-1 Inhibitors Protect Primary Mouse Islets from Cytokine-Induced Gene Changes.

Figure 2:
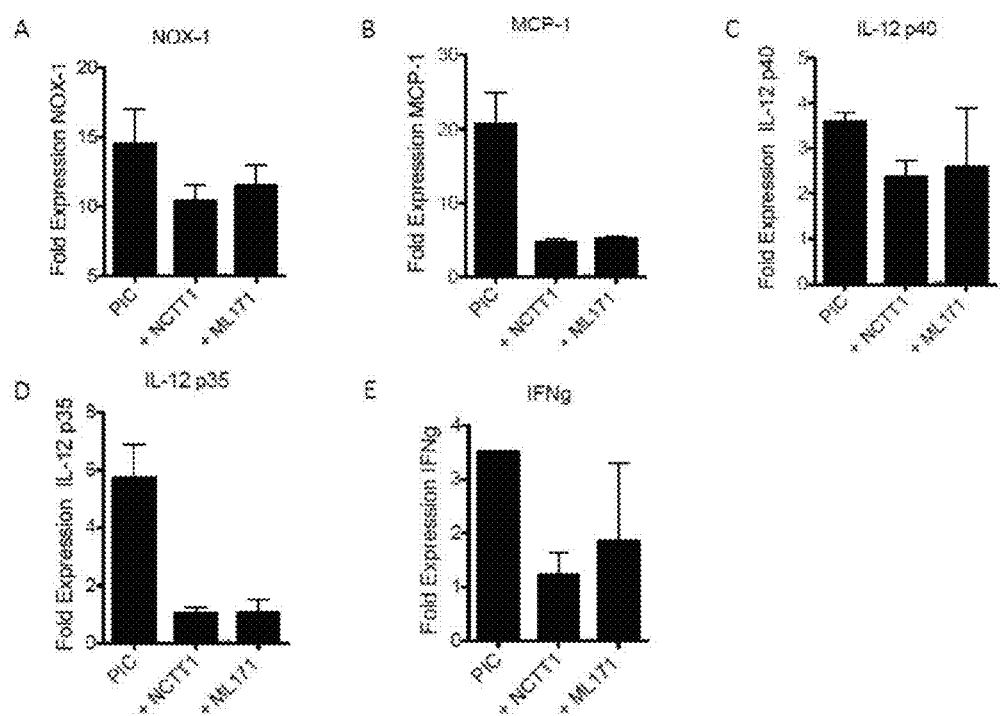
FIG. 2 is a graph showing fold induction in gene expression as a function of treatment.

FIG. 2: Treatment of primary mouse islets with inflammatory cytokines (TNFα, IL-1β, IFNγ) stimulates target gene expression. The shown genes are linked to islet dysfunction. Data is quantitative real time PCR gene expression analysis from triplicate experiments performed in replicate. Fold induction in gene expression over control (non cytokine-treated) islets is graphed. Addition of NOX-1 inhibitors (NCTT-1, 100 nM or ML171, 1 μM) attenuated the induction of genes NOX-1 (A), MCP-1 (B), IL-12p40 (C), IL-12 p35 (D) and IFNγ (F), resultant form treatment with pro-inflammatory cytokines (PIC) (TNFα, IL-1β, IFNγ).

NOX-1 Inhibitors Protect Homogeneous Rat Beta Cell Line (INS-1) from Cytokine-Induced Gene Changes.

Figure 3:
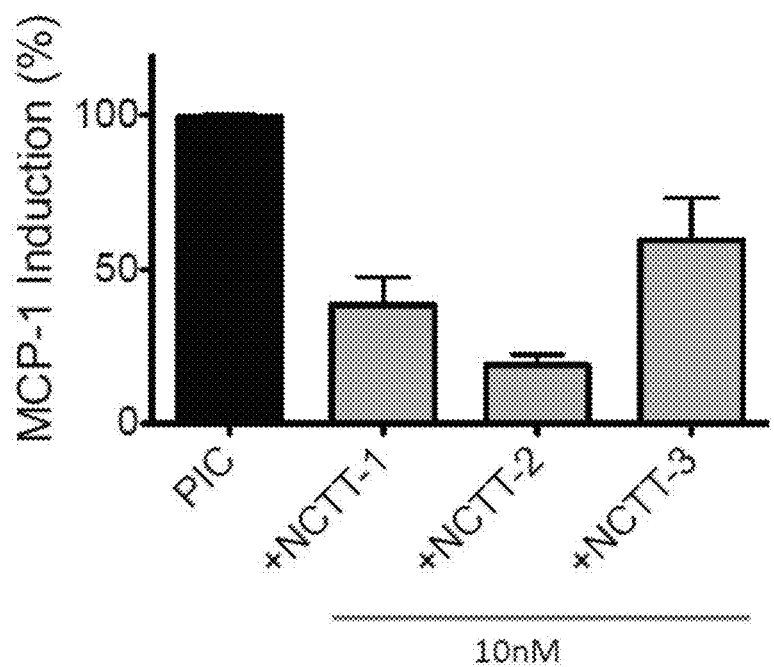
FIG. 3 is a graph of cytokine response showing that the addition of NOX-1 inhibitors (NCTT-1, -2, -3, 10 nM) attenuated cytokine-induced MCP-1 expression. NCTT-2 is Methyl-2-phenyl-5-(2-pyridinylmethyl)-1H-pyrazolo[4,3-c]pyridine-3,6(2H,5H)-dione or 5-Benzyl-4-methyl-2-phenyl-1H-pyrazolo[4,3-c]pyridine-3,6(2H,5H)-dione and NCTT-3 is a related compound with a minor structural modification on the compound class represented by C1, C2 and the GKT.

FIG. 3: Treatment of homogeneous rat beta cell line (INS-1) with pro-inflammatory cytokines (PIC) (TNFα, IL-1β, IFNγ) induced gene expression or MCP-1. Elevated MCP-1 expression is linked to islet/beta cell dysfunction. Data is quantitative real time PCR gene expression analysis from triplicate experiments performed in replicate. Percent of cytokine response is graphed. Addition of NOX-1 inhibitors (NCTT-1, -2, -3, 10 nM) attenuated cytokine-induced MCP-1 expression.

Figure 4:
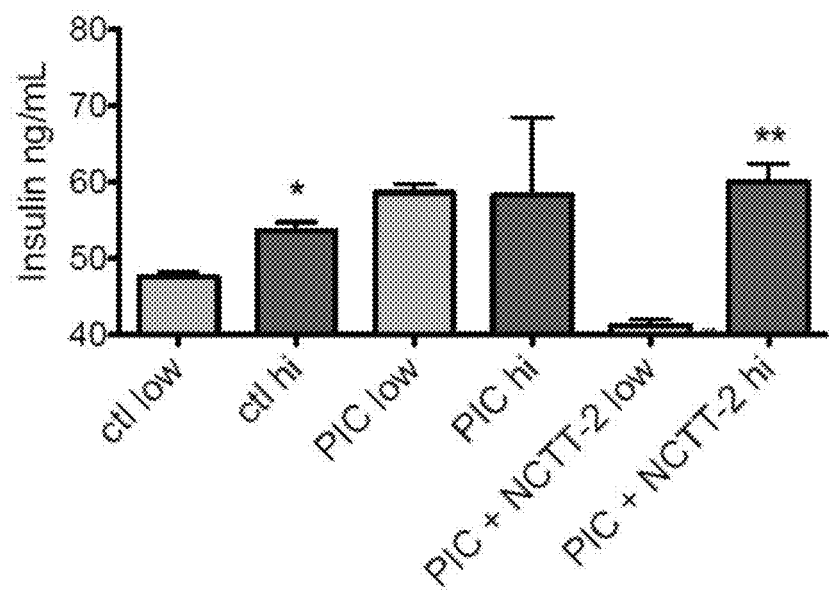
FIG. 4 is a chart showing glucose-stimulated-insulin-secretion as a result of different treatments of homogeneous rat beta cell line (INS-1).

NOX-1 Inhibition Preserves Beta Cell Function in Presence of Inflammatory Cytokines FIG. 4: Treatment of homogeneous rat beta cell line (INS-1) with pro-inflammatory cytokines (PIC) (TNFα, IL-1β, IFNγ) disrupts beta cell function measured by glucose-stimulated-insulin-secretion. Control (non cytokine-treated) cells respond to glucose elevation (low 3.3 mM to hi 16.7 mM) by increasing insulin secretion. Insulin levels are plotted. In the presence of inflammatory cytokines (PIC) this response is lost and the dysfunctional cells 'leak' insulin. Addition of NOX-1 inhibitor (NCTT-2, 100 nM) preserved the glucose stimulated insulin secretion response in the presence of inflammatory cytokine treatment (PIC). (*$p<0.05$, **$p<0.01$).

Figure 5A:
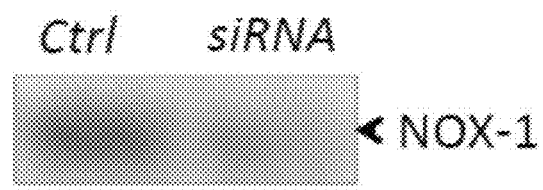
FIG. 5A confirms protein expression for NOX-1 in control (Ctrl) (untreated cells) and cells treated with siRNA (siRNA) and FIG. 5B compares the gene expression of NOX-1 and MCP-1 in pro-inflammatory cytokines (PIC) treated siRNA-deleted NOX1 cells to expression from control cells stimulated with pro-inflammatory cytokines.
Figure 5B:
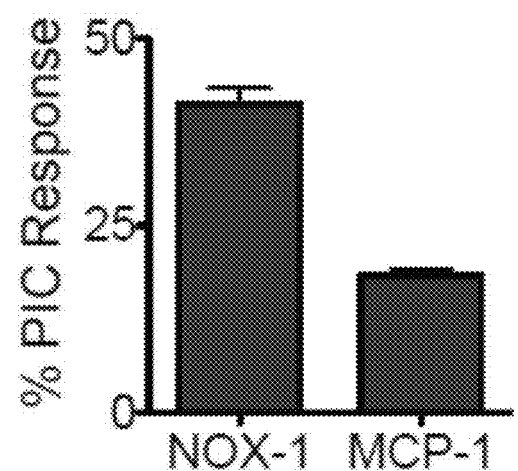

Deletion of NOX-1 Protein Expression Attenuates Inflammatory Cytokine Induced Gene Expression FIG. 5: Use of small inhibitory RNA for NOX-1 resulted in a reduction in NOX-1 protein expression in INS-1 beta cells. FIG. 5A confirms protein expression for NOX-1 in control (Ctrl) (untreated cells) and cells treated with siRNA (siRNA). In FIG. 5B, the gene expression of NOX-1 and MCP-1 in pro-inflammatory cytokines (PIC) treated siRNA-deleted NOX1 cells is compared to expression from control cells stimulated with pro-inflammatory cytokines.

Inhibition of NOX-1 Prevents Inflammatory Cytokine-Induced ROS in Beta-Cells

Figure 7A:
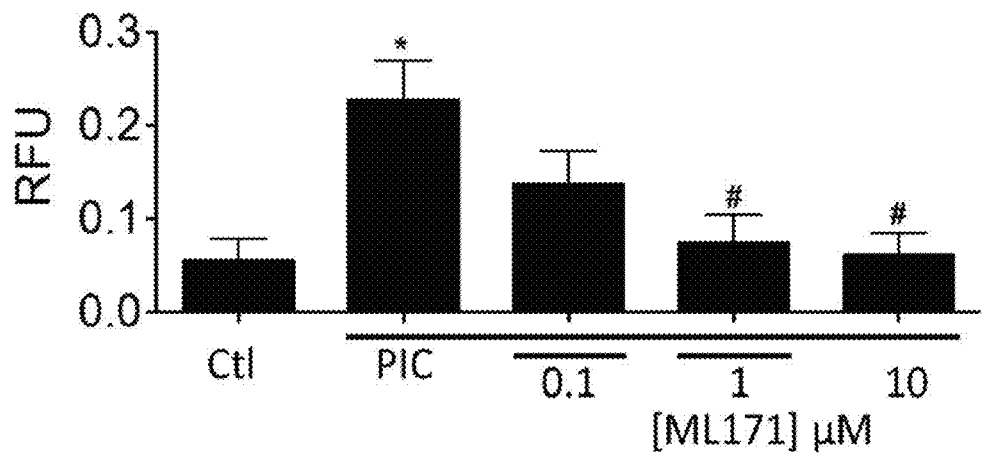
FIGS. 7A-B shows that induction of ROS by inflammatory cytokines in beta-cells is mediated by NADPH oxidase-1. INS-1 cells (FIG. 7A) and βTC-3 cells (FIG. 7B) were treated with the pro-inflammatory cytokine cocktail (PIC) of IL-1β, TNF-α, IFN-γ with or without ML171 for 1 hour. Graph shows DCFDA conversion (RFU). * p<0.05, ** p<0.01 relative to ctl, # p<0.05, ## p<0.01, ### p<0.001 relative to PIC and n=3.
Figure 7B:
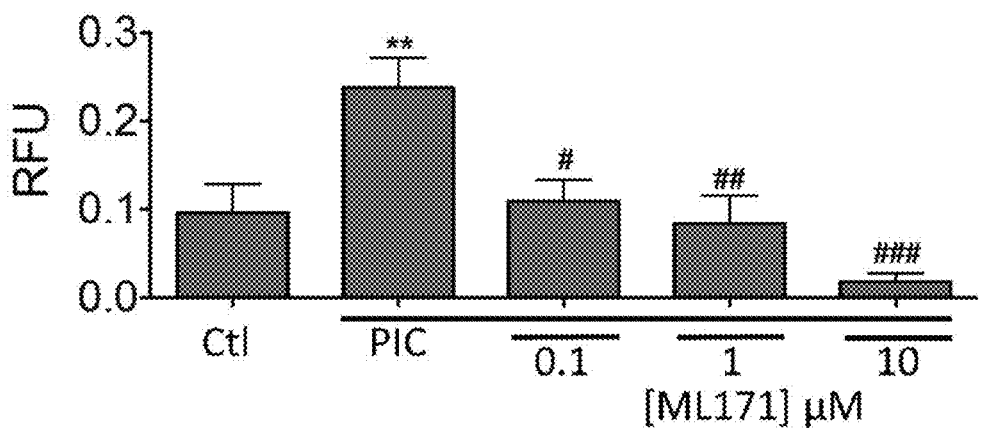

Elevation of cellular ROS in beta-cell lines INS-1 (rat beta-cell line) and βTC-3 (mouse beta-cell line) was evaluated by conversion of fluorescent substrate DCF-DA. Following one hour stimulation with a pro-inflammatory cytokine cocktail (PIC; IL-1β, TNF-α, and IFN-γ) detectable ROS elevated from control levels of 0.05±0.02 and 0.09±0.03 (INS-1 and βTC-3 respectively) to 0.25±0.04 and 0.23±0.03 (INS-1 and βTC-3 respectively). This increase was significant $p<0.05$ and $p<0.01$ (INS-1 and βTC-3 respectively). Addition of NOX-1 inhibitor ML171 resulted in a dose dependent inhibition of PIC-induced ROS in both INS-1 (FIG. 7A) and βTC-3 (FIG. 7B) beta-cells. These data identify NOX-1 activity as a contributing factor to PIC induced elevation of intracellular ROS in beta-cells.

Figure 8A:
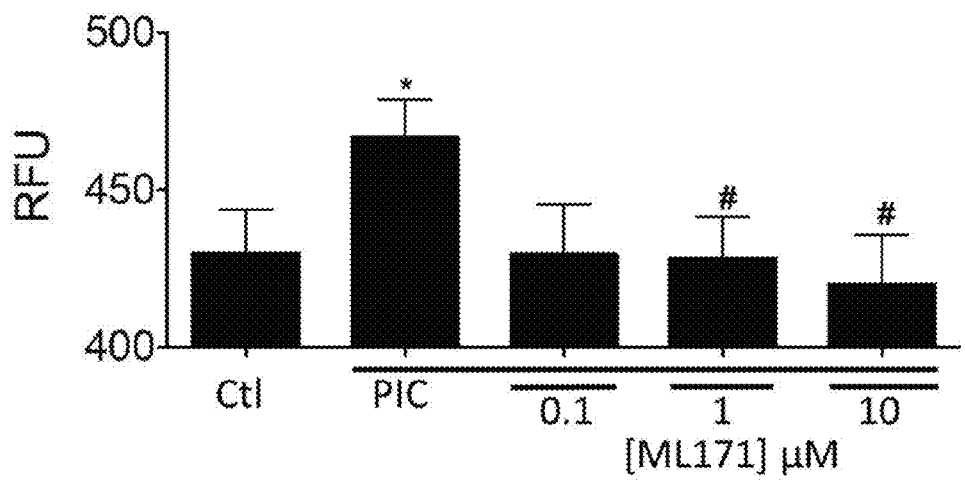
FIGS. 8A-B illustrates the protection of beta-cell lines from cytokine-induced caspase-3 activation. INS-1 cells (FIG. 8A) and βTC-3 cells (FIG. 8B) were treated with pro-inflammatory cytokine cocktail (PIC) of IL-1β, TNF-α, IFN-γ with or without ML171 for 4 hours. Graph shows pro-caspase-3 cleavage (RFU). * p<0.05, ** p<0.01 relative to ctl, # p<0.05 relative to PIC and n=3.
Figure 8B:
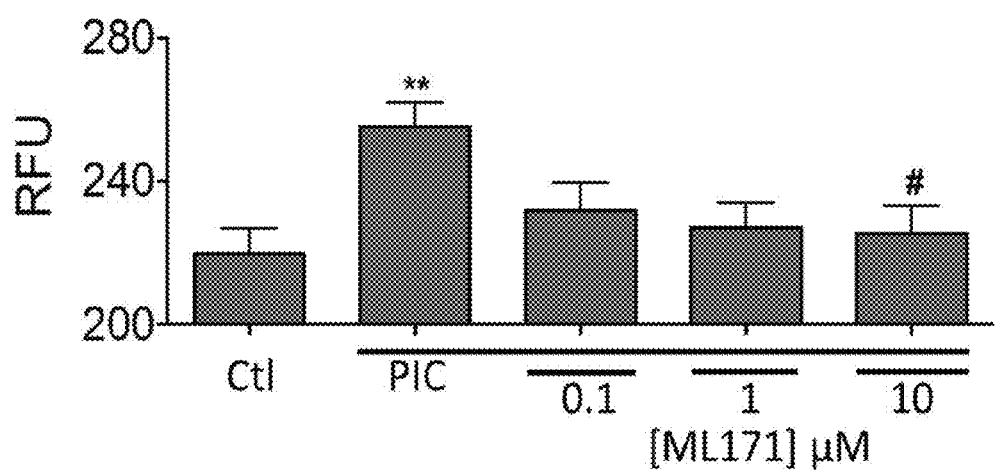
Figure 9A:
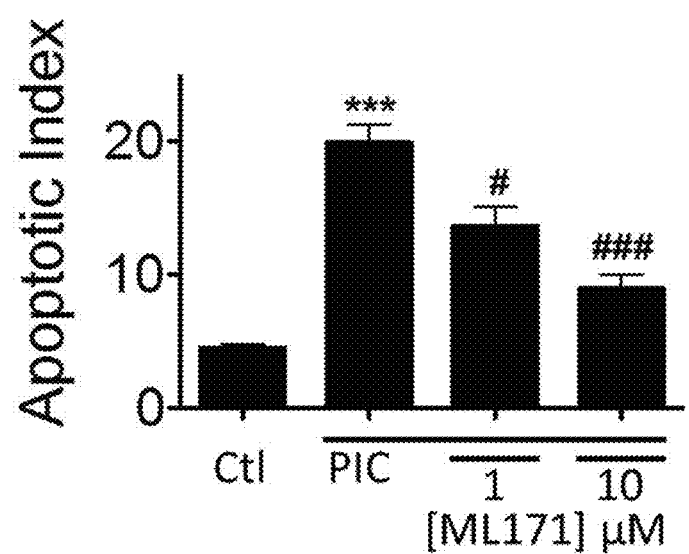
FIGS. 9A-B presents data relating to the protection of beta-cell lines from cytokine-induced apoptosis. INS-1 cells (FIG. 9A) and βTC-3 cells (FIG. 9B) were treated with a pro-inflammatory cytokine cocktail (PIC) with or without ML171 for 24 hours. Cells were examined microscopically following labeling with fluorescent viability dye YO-PRO-1 (green). Graphs for INS-1 (A) and βTC-3 (F) show quantified apoptosis from five fields per experiment. *** p<0.001 relative to ctl, # p<0.05, ### p<0.001 relative to PIC and n=3.
Figure 9B:
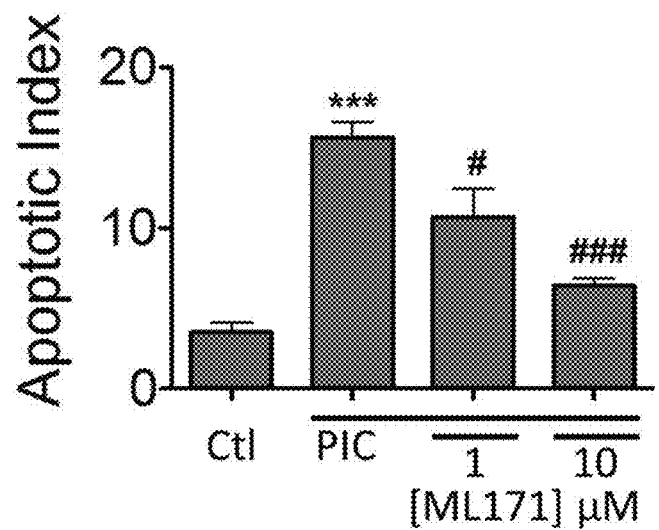

Inhibition of NOX-1 Prevents Inflammatory Cytokine-Induced Cell Death in Beta-Cells Induction of beta-cell death follows exogenous exposure to pro-inflammatory cytokines. Quantitation of caspase-3 activation was used as a measure of induced apoptosis. Caspase-3 activity increased from control levels of 430±13.74 RFU to 467±11.86 RFU following cytokine exposure in INS-1 cells and from control levels of 220±7.2 RFU to 255±6.8 RFU following cytokine exposure in βTC-3 cells. PIC-induced elevation in caspase-3 activity was significant $p<0.05$ and $p<0.01$ (INS-1 and β-TC3 respectively). Addition of ML171 blocked the PIC-induced activation of caspase-3 up to 100%±3.4% and 97%±3.1% in INS-1 (FIG. 8A) and βTC-3 (FIG. 8B) cells respectively. Induction of apoptosis was additionally studied microscopically. The fluorescent dye YO-PRO-1 (green) was used to detect cells undergoing apoptosis. Treating INS-1 and βTC-3 cells with PIC significantly increased apoptosis as shown by an increase in fluorescence as compared to control cells ($p<0.001$). Upon the inclusion of ML171 with PICs, apoptosis was significantly decreased, and both beta-cell lines were protected from cell death ($p<0.001$). Fluorescent intensity was quantitated for control, PIC, and PIC plus ML171 treatment in cell lines (FIGS. 9A and 9F).

Figure 10A:
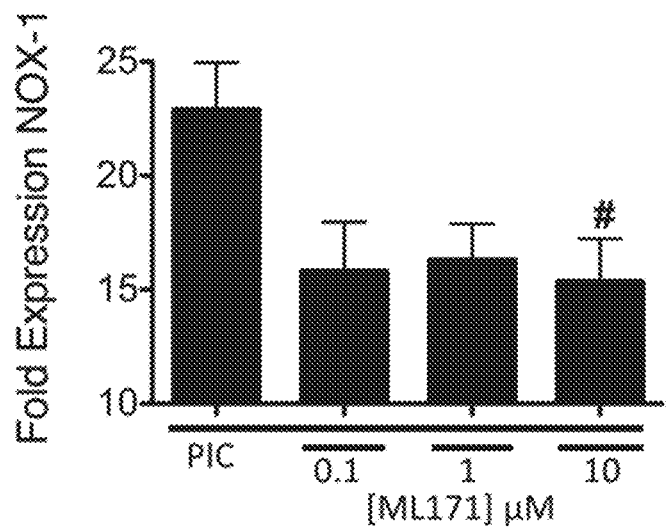
FIGS. 10A-D shows that expression of NOX-1 gene and protein production is inhibited by ML171. Shown is NOX-1 gene expression in INS-1 cells (FIG. 10A) and βTC-3 cells (FIG. 10C) following stimulation with pro-inflammatory cytokine cocktail (PIC) without or with ML171 for 24 hours. Protein expression is shown in INS-1 (rows a and b) and βTC-3 (rows c and d) for NOX-1 (rows a and c) or β-actin (rows b and c) in untreated cells (lane 1), PIC-treated (lane 2) or PIC plus 1 μM ML171 (lane 3). Graphs show densitometry of western blots from INS-1 cells (FIG. 10B) and βTC-3 cells (FIG. 10D). * p<0.05 to ctl, # p<0.05, ## p<0.01 relative to PIC, and n=3.
Figure 10B:
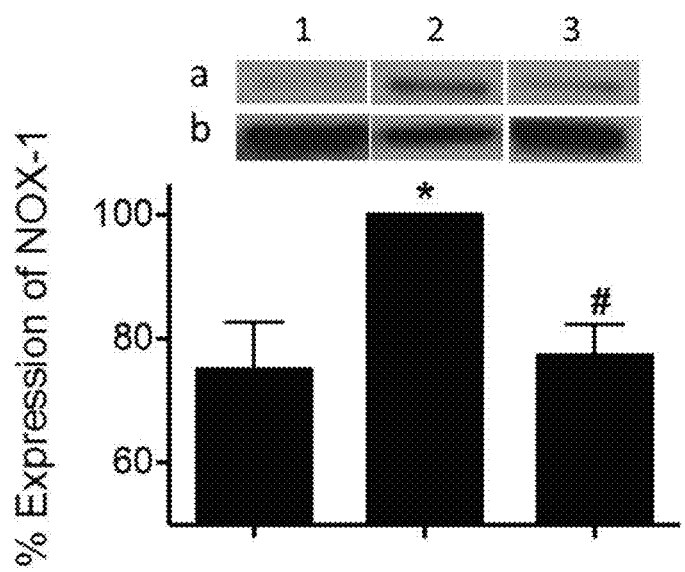
Figure 10C:
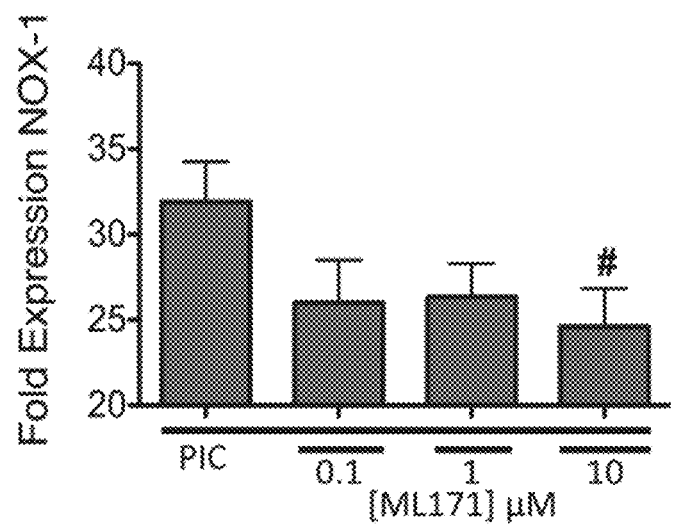
Figure 10D:
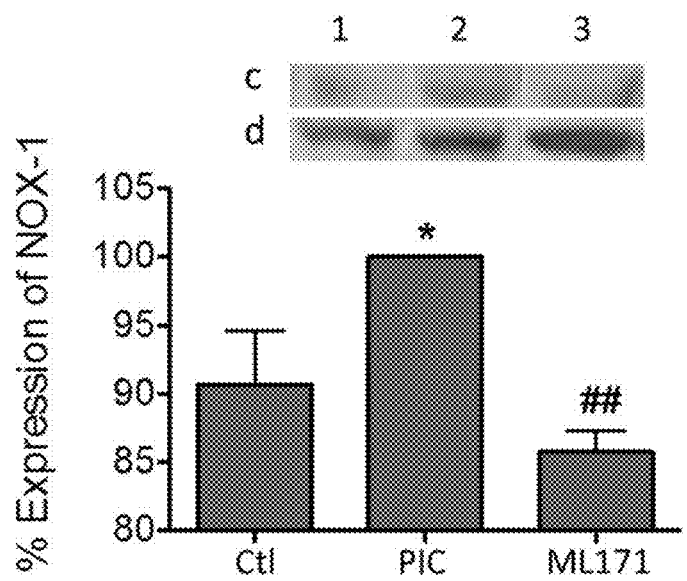

Inhibition of NOX-1 Prevents NOX-1 Gene Expression Initiated by Inflammatory Cytokine-Induced Cell Death in Beta-Cells Expression of NOX-1 gene in INS-1 and βTC-3 cells was unregulated 23±2.1 fold and 32±2.4 fold respectively (FIGS. 10A and 10C). Addition of ML171 inhibited PIC-induced expression of NOX-1 by 33% and 23% in INS-1 and βTC-3 cells respectively. Furthermore, expression of NOX-1 protein increased by 25%±0.3% in INS-1 cells and 10%±0.2% in βTC-3 cells when beta-cells were treated with pro-inflammatory cytokines (FIGS. 10B and 10D). PIC induction of NOX-1 protein was significantly inhibited by ML171 (100%±4.9% in INS-1 cells and 100%±1.5% in βTC-3 cells) ($p<0.05$ and $p<0.01$ respectively).

Figure 11A:
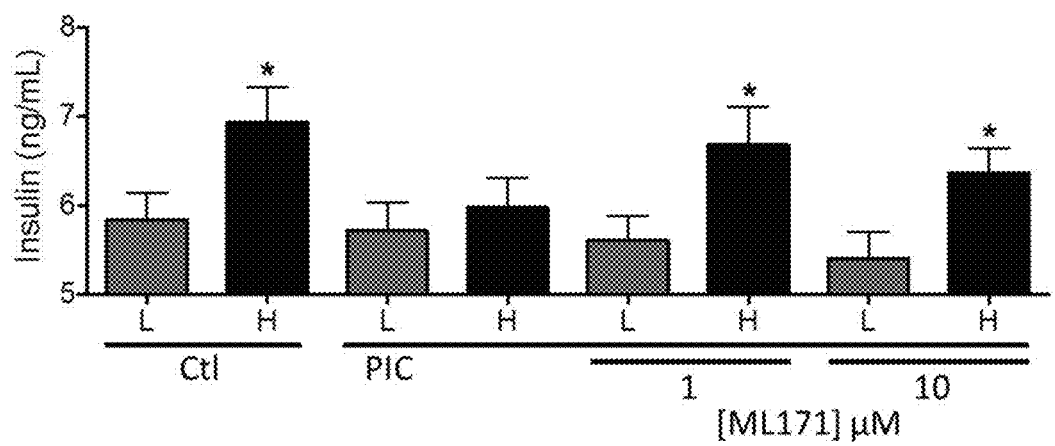
FIGS. 11A-B presents charts showing that beta-cell function is preserved by inhibition of NOX-1. Glucose-stimulated insulin secretion in INS-1 (FIG. 11A) and βTC-3 cells (FIG. 11B) for untreated cells (Ctl) or cells treated with proinflammatory cytokine cocktail (PIC) without or with ML171. Insulin secretion was measured in treated cells exposed to 1 mM glucose (L, grey bars) or 16 mM glucose (H, black bars). * p<0.05, ** p<0.01, and n=3.
Figure 11B:
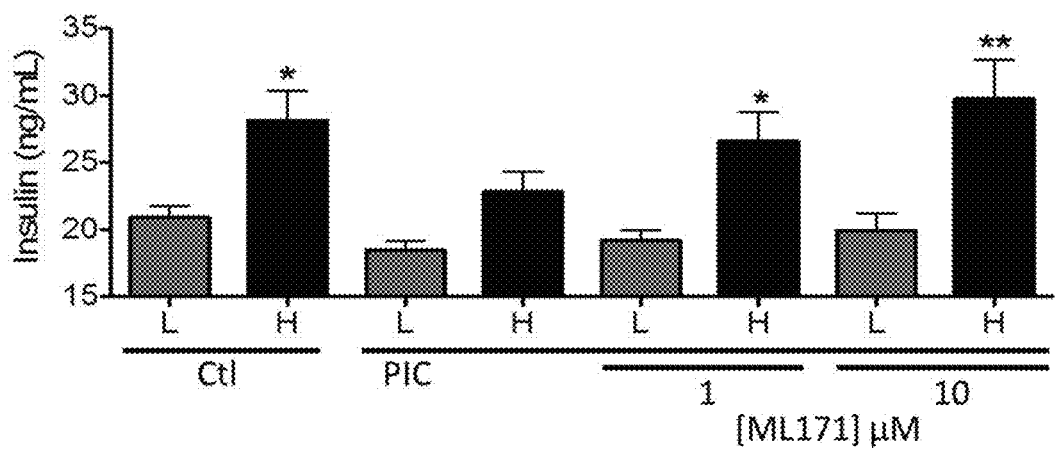

Inhibition of NOX-1 Preserves GSIS in Beta-Cells Exposed to Inflammatory Cytokines Beta-cells lines INS-1 and βTC-3 (control, Ctl) significantly increased insulin secretion when 1 mM glucose media (L) was exchanged for 16 mM glucose media (H) as shown in FIGS. 11A and 11B, ($p<0.05$). With exposure to PICs, the glucose-stimulated insulin secretion was absent in both INS-1 and βTC-3 cells. With addition of ML171 to PIC exposure, insulin secretion following exchange of low glucose media to high glucose media was significantly increased, restoring the glucose-sensitive insulin response in both INS-1 and βTC-3 cells ($p<0.05$ and $p<0.01$ respectively). These data suggest that NOX-1 inhibition by ML171 protects beta-cells from inflammation-induced cell dysfunction.

Figure 12A:
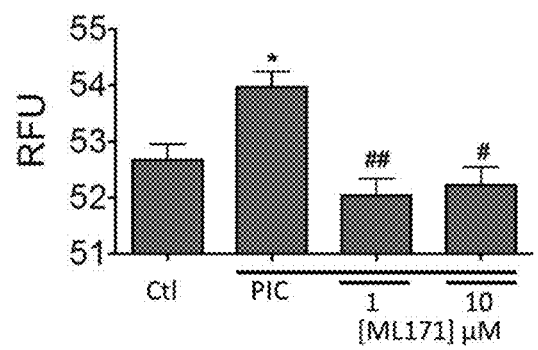
FIGS. 12A-C shows that inhibition of NOX-1 protects primary mouse islets from inflammatory cytokines. ML171 protects mouse islets from apoptosis, preserves islet function, and decreases NOX-1 gene expression.
Figure 12B:
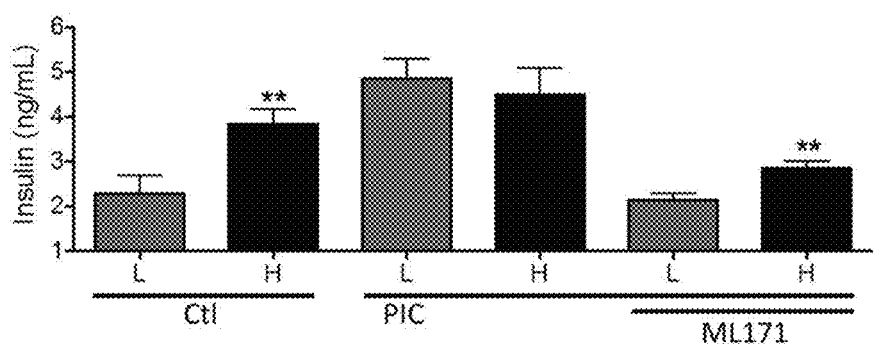
Figure 12C:
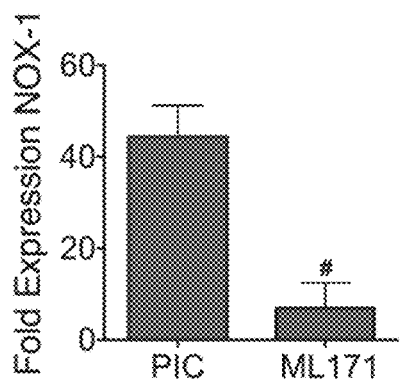

Inhibition of NOX-1 Preserves Function and Survival of Primary Mouse Islets Exposed to Inflammatory Cytokines Stimulation of primary mouse islets with pro-inflammatory cytokines resulted in cell death. Cleavage of a pro-caspase-3 substrate was used to measure cell death in isolated mouse islets. Caspase-3 increased from control levels of 52.7±0.3 to 54±0.3 following proinflammatory cytokine exposure (FIG. 12A). PIC-induced caspase-3 activity was significantly elevated ($p<0.05$). Addition of ML171 blocked the PIC-induced activation of caspase-3 up to 100%±7% and 100%±3% (1 μM and 10 μM) respectively. Beta-cell function was assessed in primary mouse islets using GSIS. Mouse islets transitioned from 1 mM glucose (L) to 16 mM glucose (H) showed a significant increase in insulin secretion ($p<0.01$) (FIG. 12B). PIC-treated islets did not exhibit a glucose-stimulated insulin response when low glucose media was transitioned high glucose media. The glucose stimulated insulin response was partially restored when islets were treated with PICs plus ML171. With inclusion of 10 μM ML171, insulin secretion was significantly increased in response to high glucose media ($p<0.01$).

NOX-1 gene expression was also measured in mouse islets. Islets treated with PICs showed a 44.4±6.9 fold increase in expression of NOX-1 gene (FIG. 6C). Addition of 1 μM ML171 inhibited PIC-induced expression NOX-1 in mouse islets by 84% ($p<0.05$).

Figure 13:
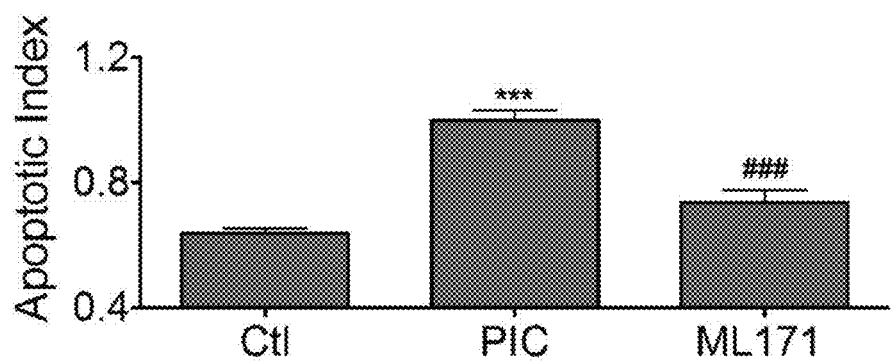
FIG. 13 presents results showing protection of primary mouse islets from cytokine-induced apoptosis. ML171 protects mouse islets from PIC-induced apoptosis. Apoptosis was measured in isolated primary mouse islets treated with pro-inflammatory cytokines without or with 10 μM ML171 for 24 hours. Cells were examined microscopically following labeling with fluorescent viability dye YO-PRO 1. The graph shows quantified apoptosis from all islets per experiment. *** p<0.001 relative to Ctl, ### p<0.001 relative to PIC and n=3.

Primary mouse islets were additionally assessed microscopically for PIC-induced apoptosis. Measured were quantitative changes in fluorescence (YO-PRO-1) relative to control cells (FIG. 13A). Following overnight exposure to PICs, a 40%±3% (p<0.001) increase in apoptosis was quantified. Inclusion of 10 μM ML171 significantly reduced PIC induced islet apoptosis by 86%±4% (p<0.001). Data presented are an apoptotic index where PIC response was set to unity (FIG. 13A).

Figure 14:
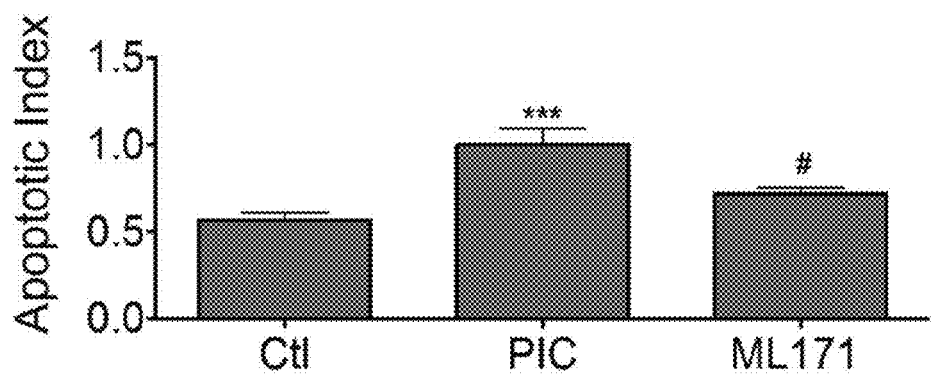
FIG. 14 illustrates protection of primary human donor islets from cytokine-induced apoptosis. ML171 protects human donor islets from PIC-induced apoptosis. Apoptosis was measured in primary human donor islets treated with pro-inflammatory cytokines in absence or presence of 10 μM ML171. Cells were examined microscopically following labeling with fluorescent viability dye YO-PRO-1 (green). The graph shows quantified apoptosis from all islets per experiment. Data is expressed as an Apoptosis Index. *** p<0.001 relative to Ctl, # p<0.05 relative to PIC and n=3.
Figure 15:
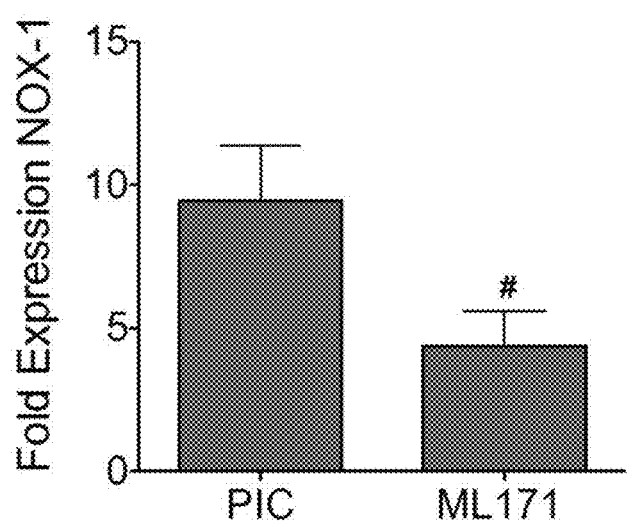
FIG. 15 shows the regulation of NOX-1 gene expression by NOX-1 activity in primary human donor islets. Expression of NOX-1 gene is shown in human donor islets treated with PIC in absence or presence of 1 μM ML171. Data shown is fold expression relative to untreated islets. # p<0.05 PIC; n=3.

Inhibition of NOX-1 Protects Human Donor Islets Exposed to Inflammatory Cytokines Primary human donor islets were treated with pro-inflammatory cytokines, and beta-cell death was measured microscopically using the fluorescent dye YO-PRO-1 (FIG. 14). Fluorescent intensity was quantified for each treatment condition (FIG. 14A). Human islets treated with PICs had a significant increase in apoptosis (44%±9%) (p<0.001). When human islets were treated with PIC plus the NOX-1 inhibitor ML171, beta-cell apoptosis induced by PICs was significantly reduced by 30%±3% (p<0.05). Data presented are an apoptotic index where PIC response was set to unity across donors (FIG. 14A). Induced NOX-1 gene expression was measured in human islets (FIG. 15). After treatment of primary human donor islets with PICs, expression of NOX-1 gene in human islets was upregulated 9.4±1.9 fold. Addition of ML171 significantly inhibited PIC-induced expression of NOX-1 by 50% (4.4±1.2; p<0.05).

Figure 16:
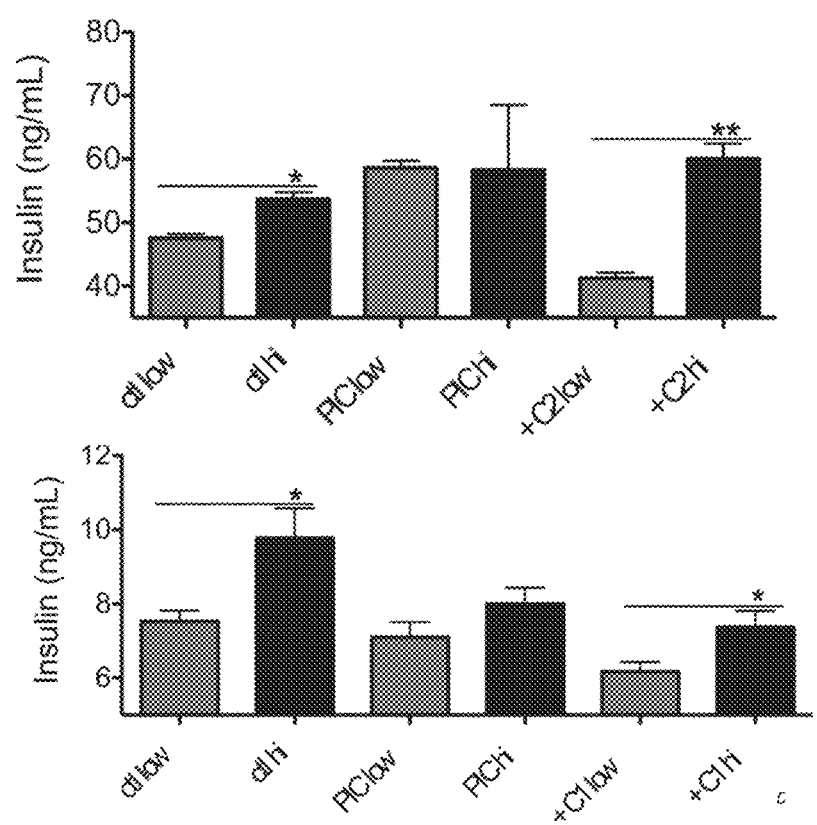
FIG. 16 is a plot of beta cell function for various treatments with pyrazolopyridine dione compounds.

Pyrazolopyridine dione compound class of dual selective NOX1/4 inhibitors were also evaluated on preservation of beta cell function and survival with concomitant exposure to inflammatory cytokines. Beta cell function was assessed by monitoring static glucose-stimulated-insulin-secretion as shown in FIG. 16. Two NOX1/4 pyrazolopyridine dione compounds C1 and C2 (Methyl-2-phenyl-5-(2-pyridinylmethyl)-1H-pyrazolo[4,3-c]pyridine-3,6(2H,5H)-dione and 5-Benzyl-4-methyl-2-phenyl-1H-pyrazolo[4,3-c]pyridine-3,6(2H,5H)-dione, respectively) were assessed at 100 nM. In control (ctl) beta cells, 16 mM glucose (hi) resulted in a significant increase in insulin secretion relative to 3 mM glucose (low). Inflammatory cytokines (PIC; IFNγ, TNFα, IL-1β)) abolished this response. The glucose-stimulated-insulin-secretion response was preserved in the presence of inflammatory cytokines by pyrazolopyridine dione compounds C1 and C2. *p<0.05, **p<0.01.

Figure 17:
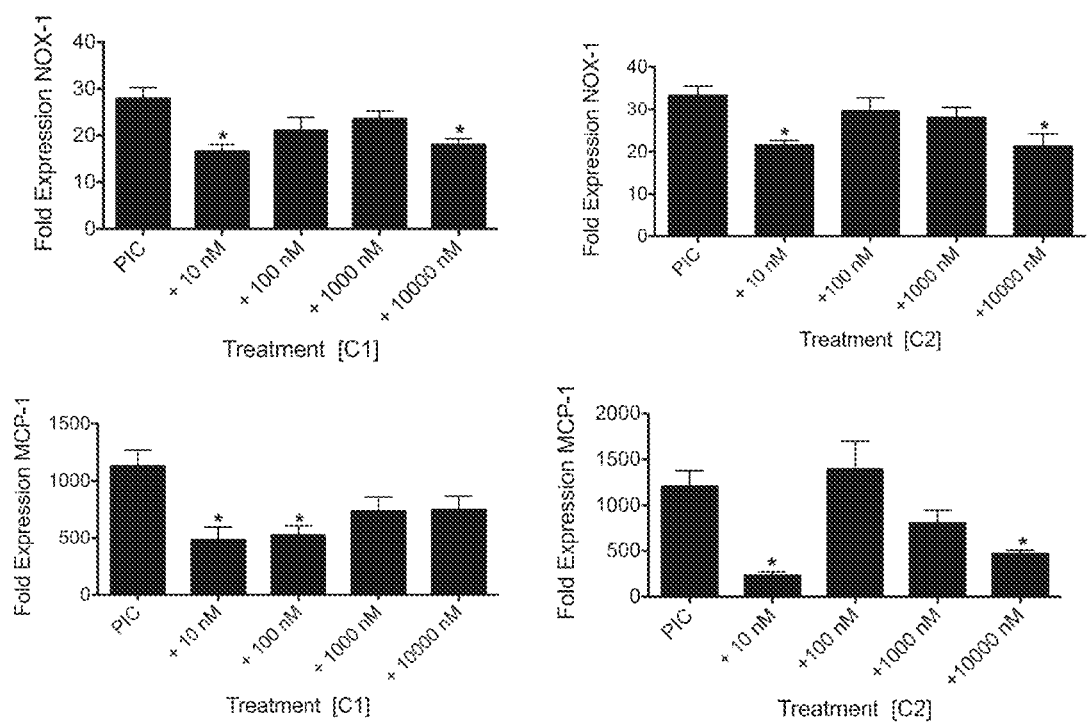
FIG. 17 presents graphs showing that pyrazolopyridine dione compounds C1 and C2 result in dose-related inhibition of inflammatory cytokine-induced gene expression fold induction in gene expression.

Inflammatory cytokines (PIC; IFNγ, TNFα, IL-1β)) induce expression of NOX-1 and MCP-1 in beta cells. Elevated NOX-1 is associated with beta cell dysfunction and NOX-1 expression is associated with feed-forward generation of reactive oxygen species. Pyrazolopyridine dione compounds C1 and C2 resulted in dose-related inhibition of inflammatory cytokine-induced gene expression as shown in FIG. 17. Shown are fold increase, *p<0.05.

Beta Cell Survival

Figure 18:
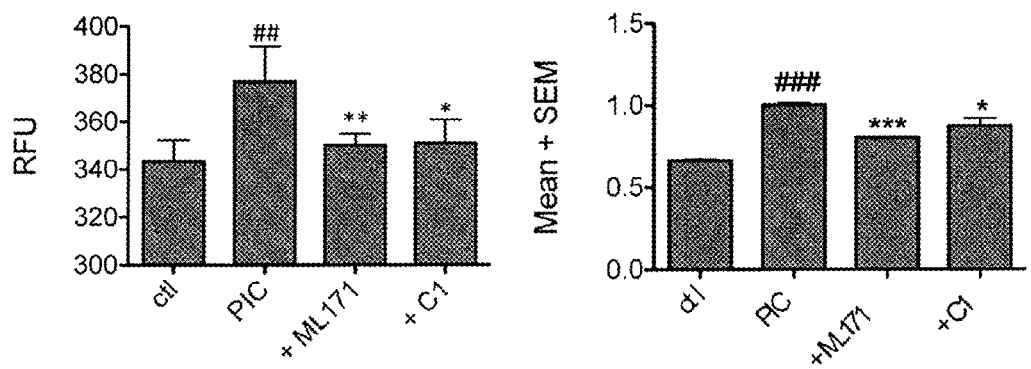
FIG. 18 is a plot of beta cell survival for various treatments with NOX-1 inhibitors.

Loss of beta cell viability in response to inflammatory cytokines was assessed by measurement of caspase 3 activation and quantified microscopy. As shown in FIG. 18, inflammatory cytokines (PIC; IFNγ, TNFα, IL-1β) induce apoptosis in beta cells. Measured by pro-caspase 3 cleavage (A) or quantified microscopy of YO-PRO-1 stained cells (B). Pyrazolopyridine dione compound C1 at 100 nM or 2-acetylphenothiazine compound ML171 at 10 μM significantly protected beta cells from inflammatory cytokine-induced cell death. Shown are RFU from fluorescent capase3 substrate, ##p<0.01 relative to control; *p<0.05; p<0.01 relative to PIC (A) and Microscopic apoptotic index ###p<0.001 relative to control; *p<0.001; **p<0.01 relative to PIC (B).

Molecular Approach to Reduce NOX-1

Figure 19:
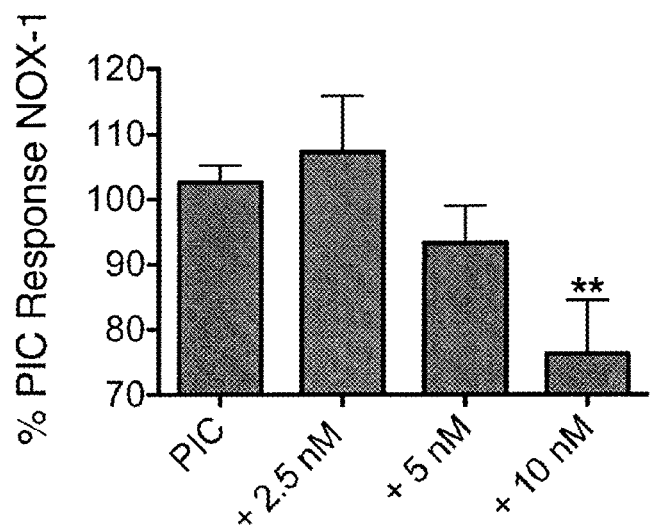
FIG. 19 shows that siRNA for NOX-1 dose-dependently reduced the NOX-1 gene activation in beta cells that results from inflammatory cytokine exposure.

Feed-forward activation of NOX-1 can also be reduced with siRNA. Inflammatory cytokines (PIC; IFNγ, TNFα, IL-1β) induce the gene expression of NOX-1 that is further regulated in a feed-forward manner involving reactive oxygen species generated by NOX-1. As shown in FIG. 19, siRNA for NOX-1 dose-dependently reduced the NOX-1 gene activation in beta cells that results from inflammatory cytokine exposure (PIC; IFNγ, TNFα, IL-1β). **p<0.01.

NOX-1 activity can be described as a mediator of inflammation-induced beta-cell dysfunction. The importance of this pathway to beta-cell pathology was reinforced with identification of a feed-forward regulation of NOX-1 in beta-cells. The present application describes the consequence of NOX-1 inhibition in terms of conferring protection to beta-cells exposed to an inflammatory environment. A chronic, albeit subclinical, inflammatory state is a recognized feature of both T1 and T2 diabetes. Study of islets and beta-cells exposed to pro-inflammatory cytokines in vitro/ex vivo have shown marked loss of beta-cell function and survival when compared to control (non-cytokine exposure). A mere acute pro-inflammatory cytokine exposure of 6 hours results in a measurable decrease in beta-cell function and elevated cell death. Cellular changes in the beta-cells concomitant with inflammatory cytokine exposure are an elevation of intracellular ROS and upregulation of genes including 12-Lipoxygenase, Monocyte chemoattractant protein-1 and NOX-1. Based on the selective upregulation of NOX-1 in beta-cells exposed to PIC and association of NOX-1 with PIC-induced islet dysfunction a selective inhibitor of NOX-1 has been sought to validate the role of NOX-1 in mediating acute inflammation induced beta-cell dysfunction.

The present application discloses compound classes with improved selectivity within the NOX family of enzymes. In addition to dual specific NOX-1/4 pyrazolopyridine dione inhibitors, a selective NOX-1 inhibitor 2-acetylphenothiazine compound termed ML171 is also useful. ML171 has an enzyme IC50 of 129-250 nM and a greater than 30-fold specificity for NOX-1 inhibition over NOX-2 inhibition and other NOX isoforms. Homogenous beta-cell lines, INS-1 and βTC-3 had a significant upregulation in intracellular ROS following acute exposure to a pro-inflammatory cytokine cocktail (PIC) of IL-1β, TNFα and IFNγ. Inclusion of the selective NOX-1 inhibitor ML171 was used to determine the importance of NOX-1 activity in PIC-induced beta-cell dysfunction. ML171 effectively decreased the elevation of intracellular ROS resulting from PIC exposure. Inhibition due to ML171 was dose dependent with protection being maximal at 10 μM. Analogous results were observed for both INS-1 and βTC-3 cells. These data suggest that a significant component of PIC-induced ROS elevation in beta-cell lines is NOX-1 dependent since induction of ROS is blocked with the selective NOX-1 inhibitor, ML171.

Association of elevated ROS and beta-cell dysfunction is established and equates to the relative low activity of ROS scavenger systems in beta-cells. PICs induce beta-cell dysfunction and cell death. We determined if these outcomes involve NOX-1 activation. Induction of cell death in beta-cell lines was evident following PIC stimulation, measured both by induction of caspase-3 cleavage or in direct quantitative microscopic analysis. Inclusion of the NOX-1 inhibitor, ML171 effectively reduced PIC-induced beta-cell death observed in INS-1 and βTC-3 cells. Equally the function of beta-cells measured by static glucose-stimulated insulin secretion is uncoupled with PIC-exposure, being preserved in the presence of ML171. Collectively, these data in homogenous beta-cells lines, demonstrate that NOX-1 activity is a major cellular event that mediates PIC-induced beta-cell dysfunction. Further, inhibition of NOX-1 can preserve function and survival in beta-cell lines exposed to inflammatory conditions.

Results in beta-cell lines were replicated in primary islets isolated from mice and human donors. Beta-cell dysfunction and cell death were observed following cytokine exposure in primary islets. Addition of ML171 protected islets from the effects of PIC for the parameters of function and cell viability measured. Significant protection was observed in mouse GSIS, cell death and caspase-3 cleavage. Relative to cell lines, the basal caspase-3 signal was reduced in primary islets; this may reflect the lower cell proliferation rate. Importantly, for the translational potential of NOX-1 inhibition, these data in primary islets provide proof-of-concept validation that disruption of NOX-1 activity is a targetable strategy to preserve islet function under inflammatory conditions.

The pyrazolopyridine dione NOX-1/4 selective inhibitors (GKT-136901, GKT-137831). GKT-136901 are reported to be well tolerated in mice with dosing 1000 mg/Kg per os. There is a feed-forward regulation of NOX-1 in beta-cells. Elevated intracellular ROS and subsequent redox signaling drive a primed NOX-1 gene. The importance of this to islet pathology is the implied potential for a reinforcing elevation in intracellular ROS and progression to oxidative stress. In terms of a therapeutic index for systemic NOX-1 inhibition, partial disruption of the feed-forward regulation of NOX-1 in betacells has the potential for therapeutic beta-cell protection with minimal off-target effects. Providing support, ML171 disrupted PIC-induced expression of NOX-1 in beta-cell lines and primary islets.

Figure 6:
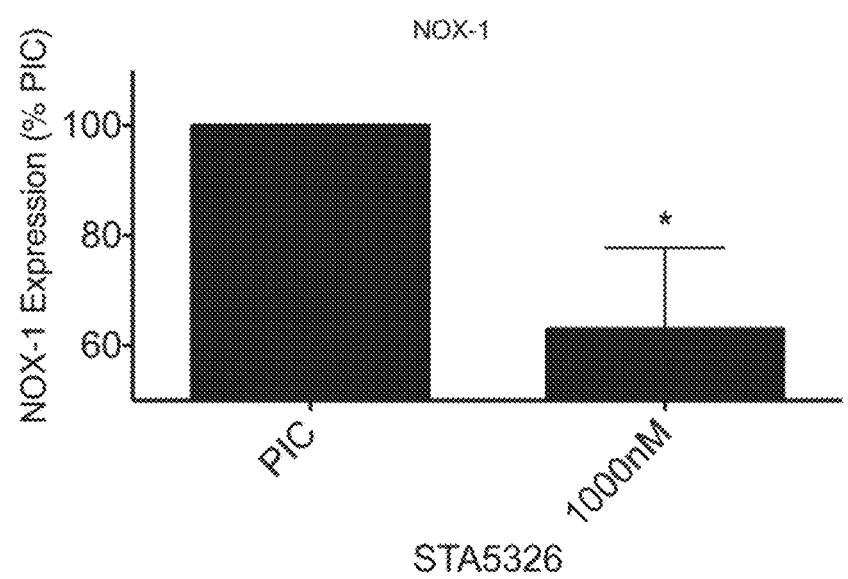
FIG. 6 shows induction of NOX-1 gene expression in beta cells by inflammatory cytokines (PIC: TNFa, IL-1b, IFNg) is inhibited by 1 μM STA 5326 (Apilimod). This compound inhibits interleukin-12 and interleukin-23 production.

Compounds that inhibit interleukin-12, interleukin-23 and/or STAT4 signaling disrupt NOX-1 upregulation by inflammatory cytokines. FIG. 6 shows induction of NOX-1 gene expression in beta cells by inflammatory cytokines (PIC: TNFa, IL-1b, IFNg) is inhibited by 1 μM STA 5326 (Apilimod).

An unaddressed clinical challenge of diabetes is establishing an effective strategy to preserve existing beta-cell mass and/or confer protection to replenished islets in an existing inflammatory environment. As described herein, NOX-1 is an effector of inflammation-induced beta-cell dysfunction. Using a selective inhibitor of NOX-1, NOX-1 is a major mediator of pro-inflammatory cytokine induced beta-cell damage. Development and translation of NOX-1 inhibitors provide novel strategies to preserve and protect beta-cell function in diabetes. These applications could include mono or combination therapies with islet regenerative agents, in addition to protection of islets pre-transplantation/xenotransplantation with or without encapsulation.

As will be apparent to one of ordinary skill in the art from a reading of this disclosure, the present disclosure can be embodied in forms other than those specifically disclosed above. The particular embodiments described above are, therefore, to be considered as illustrative and not restrictive. Those skilled in the art will recognize, or be able to ascertain, using no more than routine experimentation, numerous equivalents to the specific embodiments described herein.

The scope of the invention is as set forth in the appended claims and equivalents thereof, rather than being limited to the examples contained in the foregoing description. The contents of all of the references disclosed herein are incorporated by reference in their entirety.

I claim:

1. A method to preserve and/or protect beta cell function comprising contacting a population or preparation of pancreatic cells, beta cells and/or islets with an inhibitor of NADPH oxidase-1 (NOX-1), wherein the NOX-1 inhibitor is a pyrazolopyridine dione compound.

2. The method of claim 1 wherein the NOX-1 inhibitor is selected from the group consisting of 1-acetyl-4-methyl-2-phenyl-5-(pyridin-3-ylmethyl)-1H-pyrazolo[4,3-c]pyridine-3,6(2H,5H)-dione; tert-butyl 4-{[4-methyl-3,6-dioxo-2-phenyl-5-(pyridin-3-ylmethyl)-2,3,5,6-tetrahydro-1H-pyrazolo[4,3-c]pyridin-1-yl]carbonyl}piperidine-1-carboxylate; 1-(methoxyacetyl)-4-methyl-2-phenyl-5-(pyridin-3-ylmethyl)-1H-pyrazolo[4,3-c]pyridine-3,6(2H,5H)-dione; 4-methyl-1-(4-phenoxybutanoyl)-2-phenyl-5-(pyridin-3-ylmethyl)-1H-pyrazolo[4,3-c]pyridine-3,6(2H,5H)-dione; 1-[(3-methoxyphenyl)acetyl]-4-methyl-2-phenyl-5-(pyridin-3-ylmethyl)-1H-pyrazolo[4,3-c]pyridine-3,6(2H,5H)-dione; 1-acetyl-4-methyl-2-(2-methylphenyl)-5-(pyridin-2-ylmethyl)-1H-pyrazolo[4,3-c]pyridine-3,6(2H,5H)-dione; 1-acetyl-2-(2-chlorophenyl)-4-methyl-5-(pyridin-2-ylmethyl)-1H-pyrazolo[4,3-c]pyridine-3,6(2H,5H)-dione; 3-benzyl-7-(2-benzoxazolyl)thio-1,2,3-triazolo[4,5-d]pyrimidine; methyl-2-phenyl-5-(2-pyridinylmethyl)-1H-pyrazolo[4,3-c]pyridine-3,6(2H,5H)-dione; 5-benzyl-4-methyl-2-phenyl-1H-pyrazolo[4,3-c]pyridine-3,6(2H,5H)-dione and combinations thereof.

3. The method of claim 1 wherein the pancreatic cells, beta cells and/or islets have been exposed to a stressful stimulus.

4. The method of claim 3 wherein the stressful stimulus is selected from the group consisting of inflammation, inflammatory cytokines, high glucose, elevated free fatty acids and combinations thereof.

5. The method of claim 1 wherein the contacting step is in vitro.

6. The method of claim 1 wherein the contacting step is in vivo.

7. The method of claim 1 wherein the contacting step is ex vivo.

8. The method of claim 1 wherein the method further comprises co-administrating with another pharmaceutical agent.

9. The method of claim 1 wherein a preparation of pancreatic cells is contacted.

10. The method of claim 1 wherein a preparation of beta cells is contacted.

11. The method of claim 1 wherein a preparation of islets is contacted.

* * * * *

SEQUENCE LISTING

```
<160> NUMBER OF SEQ ID NOS: 4

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgctcccagc agaaggtcgt gattaccagg g                                  31

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggagtgaccc caatccctgc cccaacca                                      28

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
```

```
tcaccaccat ggagaaggc                                                       19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gctaagcagt tggtggtgca                                                      20
```